(12) United States Patent
Redko et al.

(10) Patent No.: US 7,982,457 B2
(45) Date of Patent: Jul. 19, 2011

(54) METHOD AND EDDY CURRENT SYSTEM FOR NON-CONTACT DETERMINATION OF INTERFACE RESISTANCE

(75) Inventors: Volodymyr I. Redko, Coral Springs, FL (US); Volodymyr Khandetskyy, Dniptopetrovsk (UA); Elena M. Shembel, Coral Springs, FL (US); Oxana V. Redko, Dnipropetrovsk (UA); Peter Novak, Ft. Lauderdale, FL (US)

(73) Assignee: Enerize Corporation, Coral Springs, FL (US)

( * ) Notice: Subject to any disclaimer, the term of this patent is extended or adjusted under 35 U.S.C. 154(b) by 298 days.

(21) Appl. No.: 12/321,075

(22) Filed: Jan. 15, 2009
(Under 37 CFR 1.47)

(65) Prior Publication Data
US 2011/0006761 A1  Jan. 13, 2011

(51) Int. Cl.
*G01R 33/00* (2006.01)
*G01R 31/302* (2006.01)

(52) U.S. Cl. ........ 324/239; 324/229; 324/242; 324/243; 324/754.21; 324/762.01

(58) Field of Classification Search ........................ None
See application file for complete search history.

(56) References Cited

U.S. PATENT DOCUMENTS

| | | | |
|---|---|---|---|
| 6,961,133 B2 * | 11/2005 | Caton et al. | 356/630 |
| 2002/0149360 A1 * | 10/2002 | Le | 324/230 |
| 2004/0070393 A1 * | 4/2004 | Sarfaty et al. | 324/230 |
| 2005/0104585 A1 * | 5/2005 | Bilik et al. | 324/240 |
| 2006/0109003 A1 * | 5/2006 | Redko et al. | 324/240 |

* cited by examiner

*Primary Examiner* — Ha Tran T Nguyen
*Assistant Examiner* — Emily Y Chan
(74) *Attorney, Agent, or Firm* — Michael G. Shariff, Esq.; Inventa Capital PLC

(57) ABSTRACT

The present invention is a method and an eddy current system for non-contact determination of the resistance between the current lead stripe and the coating during continuous fabrication of chemical power sources such as batteries, supercapacitors, photovoltaic modules and the like. Both the method and the non-destructive test system for practicing the method are described. The method includes placing of an integrated measuring transducer containing two strap-type eddy current probes above the surface of the coating applied to the metallic current lead stripe in the region of the shaft guiding the stripe movement, so that all the points of the operating surface of the transducer being at an equal distance from the stripe surface coating so that the two probes would take measurements on the same area of the coating.

20 Claims, 11 Drawing Sheets

METHOD AND EDDY CURRENT SYSTEM FOR NON-CONTACT DETERMINATION OF INTERFACE RESISTANCE

FIELD OF INVENTION

This invention relates to the field of non-destructive testing, and specifically to non-destructive testing of components and finished products in the manufacture of electrochemical power sources including batteries, supercapacitors, photovoltaic modules and the like.

BACKGROUND OF THE INVENTION

The value of the contact resistance between the metallic current lead stripe and the composite coating is among the key parameters of chemical power sources including batteries, supercapacitors, photovoltaic modules, and fuels cells.

This coating is formed by using powdered materials that have ionic conductivity, and additives of carbon, as well as soot and other materials in different combinations. The selected combinations of materials are subsequently fixed with a binder. For example, aluminum, copper, nickel, and titanium are usually used as the metal for the current leads. The specific electrical conductance of the coating is lower than that of the metal current lead by several orders of magnitude.

The value of the contact resistance between the current lead and the coating is a function of the ohmic contact area. The latter is determined by the micro-relief of the coating surface, as well as by the presence and the total area of an insulating film of aluminum oxide on the surface of the current lead. When the coating is being applied to the current lead stripe, the oxide film is substantially destroyed, while for some coatings (thin coatings of high porosity) it remains possible to partially restore this film due to the oxygen diffusion from the air through the coating layer, as well as due to the oxygen diffusion from the interior pores of the coating.

In order to determine the resistance between the current lead stripe and the coating on the fabrication line while the stripe is in motion it is necessary to use non-contact measurement methods. Any mechanical contact with the surface of the coating while the stripe is in motion would lead to the destruction of the highly porous surface of the coating at the point of contact. This effect would be exacerbated by the small thickness of the coating (10-150 µm) and the relatively low density of the coating material (1.5-3.0 g/cm$^3$).

A destructive testing method that includes cutting of test samples from finished stripe with a coating, and subsequent determination of the transient resistance between the foil and the coating by a contact method is not practical due to the following.

First, to meet the requirement of making the sampling representative, the number of test samples has to be substantial, and the samples have to be cut from different regions of the stripe. To make the test samples representative they must be removed from areas that are uniformly distributed over the entire stripe surface. The cutting out of the samples will detrimentally affect the integrity of the stripe and substantially complicate the subsequent process of fabricating the final products such as chemical power sources and supercapacitors.

Second, the contact method of measuring the specific resistance of the coating material and of the transient resistance between the foil of the current lead foil and the coating has inherent problems. For example, the coating is highly porous. Its porosity usually equals more than 20 percent, and in some cases it exceeds 50%.

Due to the presence of substantial open porosity, the surface of the coating layer features a rather complicated stochastic micro-relief. By pressing the contact area of the measuring electrode to this surface the micro-relief of the surface will be disturbed. In addition, the area of the actual ohmic contact of the coating and of the contact region will be different at each measurement thus introducing substantial errors into the measurement process.

Among the non-contact testing methods for determining the resistance between the current lead stripe and the coating, the methods of eddy currents and electrical capacitance appear, in principle, to be the best suited.

Let us review the possibility of using the non-contact electrical capacitance method. The non-contact electrical capacitance method involves using two or more coplanar wafers placed above the coating with a certain air gap, as shown in FIG. 1. The interaction between the potential electrical field of such a strap capacitor and the object being tested is well reflected by an equivalent circuit shown in FIG. 2 for a capacitor comprised of two wafers.

Since the dimensions of the wafers in the strap type capacitor substantially exceed the distance between the surfaces of wafers 101 (FIG. 1) and the surface of the aluminum foil 104, a circuit of two plane-parallel series capacitors, is actually formed.

Each of these capacitors is formed by the corresponding plate of the strap capacitor 101 and by the field-screening surface of the aluminum foil. The connection of the wafers of these formed capacitors are effected in the foil, and the connecting point of these capacitors is schematically shown at an equivalent circuit (FIG. 2), and designated as "foil".

Each of these plane-parallel capacitors contains three layers arranged in series in the field between its wafers. The capacitance of the first layer, formed by the air gap between the capacitor wafer and the coating surface, is designated on the equivalent scheme (FIG. 2) as $C_g$ (201). The second layer comprising a low-conductance coating is shown on the equivalent circuit as a chain of parallel-connected resistors $R_m$ (203) and $C_m$ (204). The third layer is comprised of the $Al_2O_3$ dielectric film formed on the surface of the aluminum foil. In the equivalent circuit scheme it is represented by the capacitor $C_d$ (202).

The thickness of the $Al_2O_3$ film is rather small, usually not exceeding ten nanometers. Therefore the value of the capacitor $C_d$ is higher by 3-4 orders than that of the capacitors $C_m$ and $C_g$. Correspondingly, the capacitive reactance of the oxide film is close to zero. Therefore it is practically impossible to determine the presence or, absence of an oxide film from the change of the total capacitance value of the strap capacitor.

In certain cases a strap capacitor with coplanar wafers can be used for determining the distance from its electrodes to the conducting surface of a sample. So, for example, according to the U.S. Pat. No. 6,593,738, for measuring the thickness of thin conducting coatings on various structures, in particular of metallic films on dielectric or semiconductor disks, the eddy current method is used. However, the eddy current probe in this case is mechanically connected to an electrical capacitance probe, which is used for determining the distance to the surface of the metallic film.

The non-contact method of eddy currents is used for measuring electromagnetic characteristics of the conducting layers and of the coatings, including thickness, and for detecting faults in the layers.

In the literature some authors proposed the use of a multiple frequency method of eddy currents for detecting corrosion in two-layer structures. They note that the eddy current method has been widely used for detecting subsurface discontinuities in the structures of aircraft. In the work described, the coil is excited by a sinusoidal alternating current (the typical frequency range is from 50 Hz to 5 MHz), which induces eddy currents in the electrically conductive material. The coil impedance is then measured.

Discontinuities, such as fissures, corrosion and surface characteristics lead to changes in the amplitude and phase of the eddy current. At the same time the eddy current signal can be distorted by a number of interfering factors that drastically complicate interpretation of the signal. With regard to multiple layer structures, such as aircraft splice joints such factors as probe deflection and skewness due to the surface deformation, change of paint thickness, simultaneously occurring discontinuities, and changes in the gap between the layers can all affect the measurements and complicate signal interpretation.

Single-frequency testing provides little information for reducing the influence of these factors. At the present time, multiple frequency eddy current testing has been successfully used for detecting hidden corrosion and subsurface cracking in aircraft lap splices. In the literature the use of the eddy current method for determining the material loss as a result of corrosion in a two-layer structure while using four operating frequencies, namely; 30 kHz, 17 kHz, 8 kHz, and 5.5 kHz is described.

The eddy current probe that rotates in a hole for fixing a multiple layer structure is described in literature. The probe output signal subject to filtration is used for detecting the presence of defects, while the probe signal not subject to filtration is used for determining the boundaries between the layers in a multiple layer structure.

The literature also describes eddy current inspection systems for nondestructive detection of faults in the region of a multiple layer conducting structure in the place of the junction of the structure. In the first of them the eddy currents are induced in the structure by an aperiodic excitation current in the induction coil. Excitation and receiving coils are used, while a change in the height of the altitude connection and of the gaps between the intermediate conducting layers in the multiple layer structure is being compensated. In this case the eddy current transducer is excited by a pulsed current while the received signals are being filtered. The presence of the air gap between the layers of the structure is indicated. As a result of filtration the parameters of the intermediate layer, the thickness of the structure being inspected are determined. Quantitative measurements of the defect parameters are obtained by comparing the signal value with the calibration curve. The Fourier transformation of the signals is used for obtaining the amplitude-frequency characteristics. A frequency filtration is used.

A device and a process for nondestructive determination of changes of the ohmic resistance of a thin layer by using eddy currents have also been described. The induction coil is excited by a high frequency current. Its magnetic field induces eddy currents in the layer thus weakening the magnetic field of the coil. The coil forms a part of the generating circuit that is constantly maintained in the resonance by using phase correcting circuits. Under such resonant conditions, the reactive parts of the generating circuit may be neglected, and the current flowing in the generating circuit depends exclusively on the ohmic resistance of the induction coil, the changes in which determined by the ohmic resistance of the layer being tested.

The use of a parallel resonant circuit connected to the harmonic oscillations generator for measuring the electrical conductance of the media is also described in patent FR2782802A1.

Other researchers have described a method for eddy current testing of a minimum of one layer placed on a substrate. A minimum of one layer or the substrate conducts electric current. An inductance coil is used as a primary field source or to measure the secondary field parameters arising from the eddy currents induced in the conducting layer or in the substrate. The primary magnetic field is generated at a minimum of two frequencies. The measured values of the added impedance are used for determining the electromagnetic properties of the substrate and the layer, as well as the layer thickness.

An eddy current method for testing multiple layer coarse grain weld seams for the absence of defects has also been described in literature. It is noted that the detection of cracks in a weld seam is complicated due to the coarse grain material in the seam. U.S. Pat. No. 6,524,460 describes a method for determining the characteristics of metallic electrodes in ceramic sensors wherein the metallic electrodes are sprayed as layers and are subjected to subsequent annealing. The purpose of the invention, according to the patent description, is to develop a simple nondestructive and efficient method that allows automation of the sensor acceptance inspection process.

In accordance with the proposed testing procedure, the quantity and distribution of the sprayed gold, due to the fact that it is placed in the protective layer, is determined indirectly. This is done by measuring the layer thickness during the process of manufacturing the electrode, and of respective comparison procedures by means of the eddy current measuring process. To this end the electrode is placed in the magnetic circuit of the coil that is fed with the high frequency current, and the resulting impedance of the coil is measured using the LCR of the measuring circuit. It is noted that the coil can be switched into the resonant circuit by means of a capacitor.

A number of patents deal with the use of two eddy current probes usually operated at different frequencies for measuring the properties of lamellar conducting objects while various procedures for correcting the measurement signals are being used.

The eddy current method is also used for inspecting anomalies in conducting wafers. The excitation and the receiving coils placed at different edges of the wafer initially pass the electromagnetic energy in one direction, from the excitation coil to the receiving coil, then the excitation and the receiving coils change their roles and the energy of the magnetic field is passed in the reverse direction. As a result the defects are detected at an approximately equivalent sensitivity irrespective of the depth of their location in the wafer. The probes generate a periodic magnetic field. The excitation coil and the auxiliary unit direct the electromagnetic field into the wafer being inspected. In an alternative design the auxiliary unit is comprised of a coil controlled by a signal that has a phase and amplitude related to the corresponding signal parameters of the excitation coil. Laminated screens are also used for focusing the electromagnetic energy.

An eddy current measuring transducer containing measuring and compensating probes manufactured in the form of cylindrical induction coils, as well as a measuring circuit has been described. This system is intended for determining the material properties of the object being tested and its geometrical parameters. The measuring transducer operation method includes placing the object at a specified distance from the measuring and the compensating probes, measuring the impedance of the measuring probe at the first and second specified frequencies, determining the material properties, as well as the geometric parameters of the object, on the basis of the impedance measurements, while compensating the temperature influence on the measuring probe by means of the signal being formed by the compensating probe. The compensating probe is spatially smaller of the measuring probe and is located inside the latter. The turns of both probes are co-axial and their geometrical shape is identical. The compensating probe is placed so that the influence thereon of the object being tested is minimal.

The temperature compensation is comprised of subtracting the integrated impedance of the compensating probe from the integrated impedance of the measuring probe. For determining the material properties, as well as the geometric parameters of the object, the latter is initially placed at a distance from the measuring probe that exceeds the probe diameter while the impedance of the measuring probe is being determined. Then the object is brought closer to the measuring probe and its impedance is measured again. The obtained values form a basis for determining the added impedance of the probe which is used for determining the electrical conductance and the geometric dimensions of the object taking into account the correction being used.

The analysis of the patent information and technical literature show that the eddy current method has been widely used for non-contact measurement of the electromagnetic properties and the thickness of layers in lamellar structures and detection of faults in the layers.

However, no patents have been found that deal with the non-contact measuring of the contact resistance between the metallic foil and the thin low-conducting composite coating, the electrical conductance of which can change depending on density, a change in the concentration of its components, granulometric composition (granularity), and homogeneity of the composite mass after mixing of the components.

SUMMARY OF THE INVENTION

The present invention involves an eddy current method for non-contact evaluation of the resistance between the metallic current lead stripe and the low conductance composite coating during the process of fabricating chemical power sources, including batteries, supercapacitors, photovoltaic cells and the like.

The present eddy current method is used for non-contact determination of the resistance between the metallic current lead stripe and the low conductance composite coating during the process of fabricating chemical power sources.

According to the present invention, an integrated measuring transducer comprising two eddy current probes joined into an integral structure is arranged above the surface of the coating on the metallic current lead stripe, in the region of the stripe movement guide shaft, so that all the points on the operating surface of the transducer are found at an equal distance from the stripe surface.

The first eddy current probes wound with parallel conductors having identical direction of the currents in the lines along its operating surface. The conductors are arranged along the direction of the current lead stripe motion. The added real components of probe resistance normalized relative to its own induction impedance are used as a signal. The operating frequency of the first probe is selected according to the frequency dependence minimum of its relative added real components of resistance.

The second eddy current probe on its operating surface also contains parallel conductors, but with an opposite direction of the currents in adjacent wires. The added real components of probe impedance is normalized relative to its self induction impedance is also used as a signal from the second probe. The operating frequency of the second eddy current probe is selected in the post-extremum region of the hodograph added by the current lead stripe without covering the impedance, so that the value of the added real component of impedance would equal not more than 10% of the maximum value.

Using the added impedance component values of the second probe that were obtained by measuring on the current lead stripe without a coating and with a coating, and the subsequent procedures of the additive and multiplicative adjustment, the value of the relative added real components of resistance of the second probe is detected. This arises only from the eddy currents passing in the coating layer.

The measurements of the first and of the second probes are synchronized taking into account the uniform movement rate of the current lead stripe with a coating so that both probes would perform measurements on the same region of the coating.

The value of the relative added real components of resistance of the first probe is adjusted using the detected values of the added real components of complex impedance of the second probe. The value of the contact resistance between the current lead stripe and the coating at different regions is evaluated in the process of the stripe movement using the adjusted values of the relative added real components of complex impedance of the first eddy current probe.

The frequency characteristics of the relative added real component of the impedance of the first probe is measured by placing it over the surface of the current lead stripe that has no coating and is arranged on the guide shaft at a distance that equals the sum of the installation gap and the coating thickness values. The first probe is positioned over the coating surface on the current lead stripe arranged on the guide shaft at a distance that equals the installation gap value, and the frequency characteristics of the relative added real components of complex impedance are measured again. The frequency that corresponds to the minimum frequency characteristics of the relative added real components of impedance is determined while the first probe is placed above the coating on the current lead stripe that is accepted as the operating frequency of the first probe. The relative added real components of complex impedance of the first probe obtained when it is placed over a lead stripe without a coating and is determined corresponding to the operating frequency is stored and is subsequently used as a reference value. During the process of measurements the difference of the relative added real components of complex impedance of the first probe placed over the moving current lead stripe with the coating is determined, as is the reference value that forms a signal of the first probe.

The operating frequency of the second eddy current probe is limited at the high end by the boundary frequency that is three times lower of the own resonant frequency of the probe.

The second probe is positioned over the surface of a current lead stripe that has no coating and is placed on the guide shaft at a distance equal to the sum of the installation gap and the coating thickness values, and the value of the relative added real components of complex impedance of the probe is measured at its operating frequency. Then the second probe is again positioned over the surface of the current lead stripe without a coating at a distance that equals the coating thickness, and the value of the relative added inductance of the probe is measured at its operating frequency. Thereafter, the second probe is installed directly on the surface of the current lead stripe without coating that is found on the guide shaft, and the relative added inductance of the probe is measured at the boundary frequency.

The difference of the values of the relative added inductance of the second probe is determined, the values being measured on the current lead stripe with a zero gap at the boundary frequency, and with an air gap equal to the coating thickness, at the operating frequency. From the values of the relative added real components of complex impedance of the second probe placed over the moving current lead stripe with a coating is subtracted the analogous value measured at the operating frequency while the second probe is positioned over the surface of the stripe with no coating at a distance that equals the sum of the installation gap and the coating thickness values, thus performing an additive updating. The additively updated complex impedance values of the second probe are divided by the obtained difference of the relative added inductance values of this probe, thus performing a "multiplicative" updating. Using the updated values and taking into account the installation gap value, the values of the relative added real components of complex impedance of the second probe that are caused by the eddy currents passing only in the coating layer are obtained.

Before starting the measurement cycle, the multiple measurements, with not less than 200 measurements being recommended, by using the second probe on the current lead stripe with a coating in order to determine the initial average value of the relative real components of complex impedance added by the currents of the coating, which is then refined during the remainder of the measurement cycle. The signal of the first eddy current probe is corrected by multiplying it by the coefficient $\gamma = R_{ad}/R_{ad}^{(av)}$ that represents a relation of the real components of complex impedance of the second probe added by the coating currents to its current average value.

Before starting the measurement cycle, the multiple measurements with not less than 200 measurements being recommended to be taken on the current lead stripe to determine the initial maximum value of the first probe signal corrected by the second probe signal which is then refined during the remainder of the measurement cycle.

The value of the contact resistance between the current lead stripe and the coating is evaluated relative to the updated values of the maximum signal of the first probe to the signal at the given control position or location, which is proportional relative to the contact resistance at the given control position to its averaged minimum value. A tolerance value is specified, which is the upper boundary of the range within which a change of the relative value of contact resistance is allowed. Using the present invention, quality control can be carried out by indicating relative contact resistance value increase beyond the allowed tolerance range by applying marks onto the coating surface in various colors according to the degree to which the upper tolerance limit is exceeded.

BRIEF DESCRIPTION OF DRAWINGS

Shown in the drawings are embodiments of the present invention that are presently preferred. However it is understood that the invention can be embodied in other forms without departing from the spirit or essential attributes thereof.

DETAILED DESCRIPTION OF THE INVENTION

Figure 1:
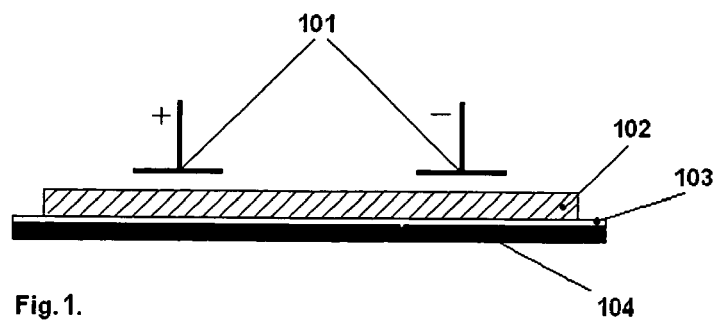
FIG. 1 represents a strap capacitor with two coplanar wafers arranged over the current lead stripe with a coating: 101 is the strap capacitor wafers, 102 is the coating, 103 is the insulating oxide film on the surface of the current lead stripe (foil), 104 is the current lead stripe (foil).
Figure 2:
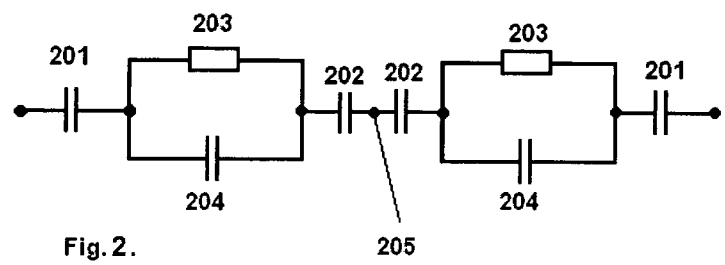
FIG. 2 depicts the equivalent circuit of a strap capacitor arranged over the coating on the current lead stripe: 201 is $C_g$, the capacitance of the air gap between the corresponding capacitor wafer and the out surface of the coating, 202 is $C_d$, the capacitance of the $Al_2O_3$ dielectric film on the surface of the aluminum foil; 203 is $R_m$, and 204 is $C_m$: the resistance and capacitance, respectively of the coating in the direction perpendicular to the surface.

The device of the present invention for non-contact evaluation of resistance between the current lead stripe and the coating includes:
  resonant means for measuring the relative added real components of the complex impedance of the first eddy current probe at its operating frequency;
  resonant means for measuring the relative added real components of the complex impedance of the second eddy current probe at its operating frequency;
  means for measuring the relative added inductance of the second eddy current probe at the operating and the boundary frequencies;
  means for three-channel analog-to-digital conversion of signals;
  a data storage unit;
  means for synchronizing the measurements of the first and the second probes; unit for determining the difference of the relative added real component of impedance of the first probe and the reference signal;
  unit for determining the difference in values of the relative added inductance of the second probe measured on the current lead stripe with a zero gap at the boundary frequency and with an air gap equal to the coating thickness, at the operating frequency;
  unit for additive updating of the relative added real components of the complex impedance of the second eddy current probe;
  unit for multiplicative updating of the relative added real components of the complex impedance of the second eddy current probe;
  unit for current averaging of the updated values of the relative added real components of the complex impedance of the second probe;
  unit for updating the difference in the relative added real components of the complex impedance of the first probe and of the reference signal while using the updated signal values of the second probe;
  unit for determining the maximum updated difference for the first probe;
  unit for evaluating and recording the contact resistance between the current lead stripe and the coating at the test position or location;
  unit for detecting and indicating the output beyond the tolerance limit;
  digital-to-analogue converter;

unit for marking the defect zones on the surface of the coating.

The first and the second eddy current probes form an integral structure and are arranged therein in series relative to the stripe movement while their common operating surface forms a part of the surface of a cylinder with a rectangular scanning, and is limited in its width by the maximum width of one of the probes, and in its length by the overall length of the probes taking into account the distance there between. The total operating surface of the probes is coaxial to the surface of the current lead stripe in the region of the shaft guiding the movement of the stripe.

The shell of the first eddy current probe forms in section a rectangle while its operating surface is formed by the concave surface of the shell that is closest to the coating, with the placed thereon with constant spacing parallel unidirectional current lines while its non-operating surface is formed by the convex surface of the shell on which the oppositely directed parallel current lines are found. The winding of the second eddy current probe is concentrated on the concave surface of the shell that is the closest to the coating and comprises a set of parallel current lines with oppositely directed currents in the adjacent lines and with a constant distance there between.

The distance between the current lines of the first probe is selected taking into account the necessity of providing the maximum stability of the vector potential of the probe field within the control zone. The distance between the current lines of the second probe is selected taking into account the necessity of reducing to a minimum the influence of the current lead foil on the value of its added real components of the complex impedance. The relation of the length of the current lines located on the operating surfaces of the first and the second probes to the distance between the current lines is not less than 10. The distance between the end of the first probe and the beginning of the second is not less than the double width of the shell section of the first eddy current probe.

In case the current lead stripe has a coating on both sides, a pair of identical integrated measuring transducers is used, each one being located in the vicinity of its guide shaft, but over a opposite sides of the stripe coating. In such case each transducer of the pair is located at the same distance from the lateral edge of the current lead stripe. Several integrated measuring transducers are placed over the coating surface on the current lead stripe and are fixed on one generatrix arranged perpendicularly to the lateral edge of the current lead stripe, with the distance between the transducers being equal. In case the coating is provided on both sides, several pairs of measuring transducers are used, while the transducers arranged over one side of the coating and the transducers arranged over the opposite side are fixed on separate generatrices arranged perpendicularly to the lateral edge of the stripe. The minimum distance between the lateral edge of the integrated measuring transducer and the lateral edge of the coating on the current lead stripe is not less than the height of the first eddy current probe, while the distance between the closest to one another lateral edges of the integrated transducers is not less than twice the height of the first eddy current probe.

The unit for marking the faulty zones within which the relative value of the contact resistance between the current lead and the coating exceeds the limits of the specified tolerance, putting marks for each integrated measuring transducer separately by different colors corresponding with the degree to which the upper tolerance limit of the contact resistance value is exceeded.

An integrated measuring transducer contains two strap type parametric eddy current probes joined into an integral structure and arranged therein in sequence relative to the stripe movement. The integrated measuring transducer is placed over the surface of the coating found on the metallic stripe (foil) of the current lead in the region of the circular cylindrical shaft guiding the stripe movement. The operating transducer surface comprising the common operating surface of the first and the second eddy current probes is cylindrically shaped and has a rectangular section.

Figure 3:
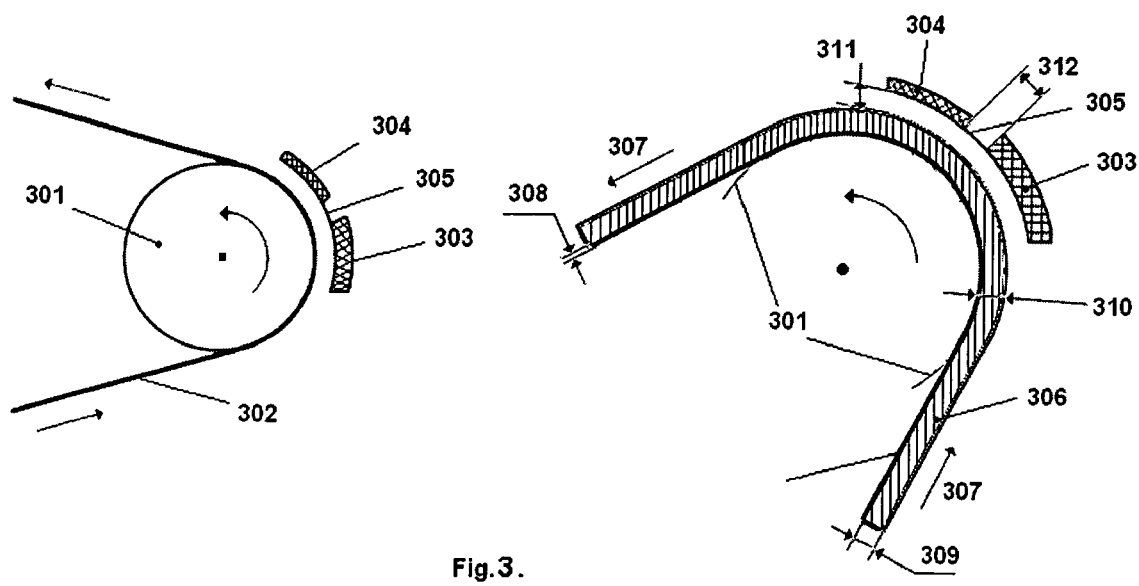
FIG. 3 shows a schematic arrangement of eddy current probes relative to the current lead stripe with a coating (the figure on the right is an enlarged variant of the left figure): 301 is the shaft that guides the current lead stripe movement, 302 is the current lead stripe (foil), 303 is the first eddy current probe, 304 is the second eddy current probe, 305 is the common shell for fixing the probes; 306 is the composite coating on the current lead stripe; 307 is $V_0$, the speed of the current lead stripe movement; 308 is $T_f$, foil thickness; 309 is $T_c$, the coating thickness; 310 is $T_f+T_c$; 311 is $d_0$, the installation gap value of the probes relative to the outer surface of the coating; 312 is $l_0$, the distance between the probes on their common shell.

Across its width, in the direction perpendicular to the stripe movement, this surface is limited by the maximum width of one of the probes. Along its length, in the direction of the stripe movement, this surface is limited by the total length of the probes taking into account the distance between them. All the points of the operating surface of the integrated measuring transducer are at an identical distance from the stripe surface. Thus the transducer operating surface is coaxial to the stripe surface in the region of the guide shaft. The relative position of the eddy current probes and of the current lead stripe with the coating are schematically shown in FIG. 3.

Figure 4:
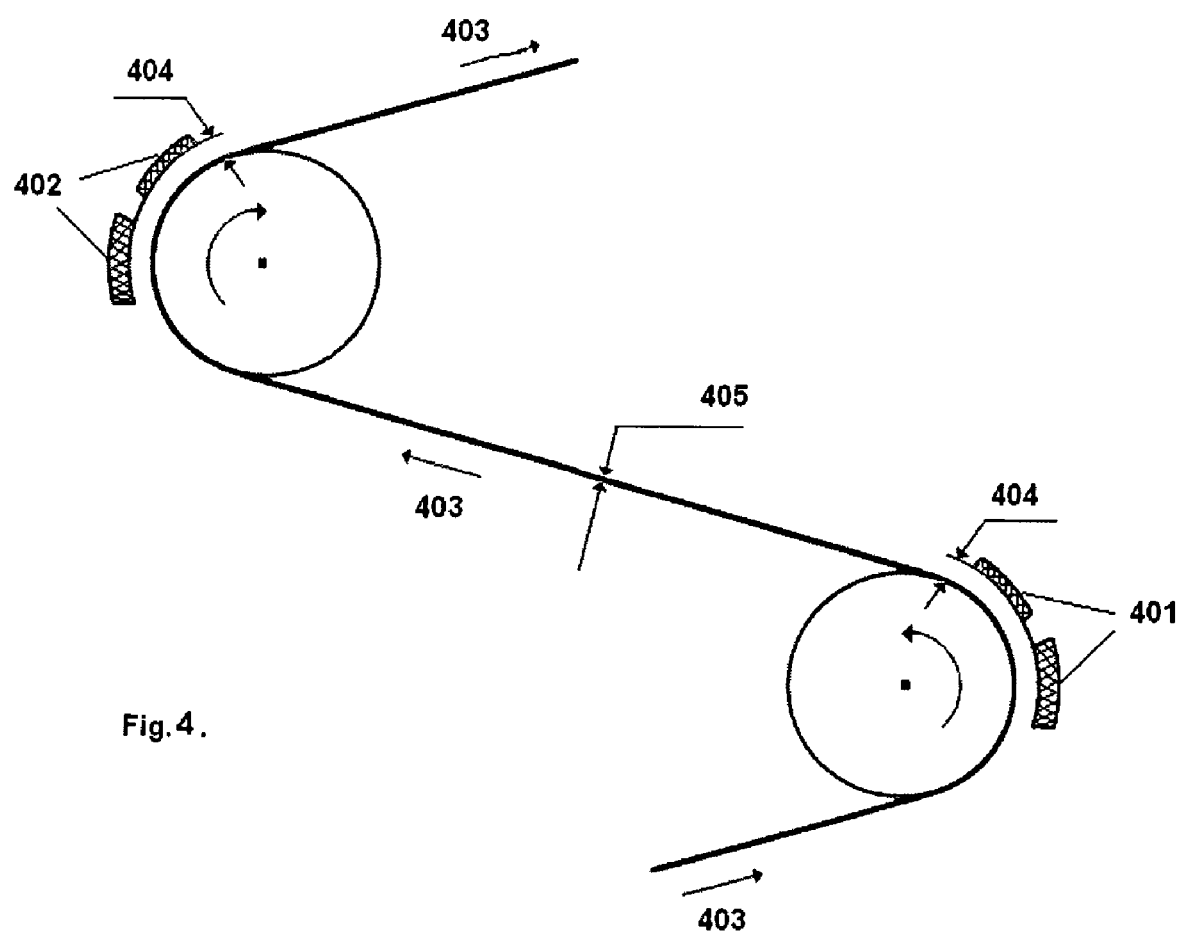
FIG. 4 shows a schematic arrangement of the integrated measuring transducers for the case of the two-sided coating of the current lead stripe (foil): 401 is the first integrated transducer containing two eddy current probes, 402 is the second integrated transducer containing two eddy current probes, 403 is $V_0$, the speed of the current lead stripe movement; 404 is $d_0$, the installation gap value of the probes relative to the outer surface of the coating; 405 is the sum of the $T_f$, foil thickness and $T_c$, coating thickness.

In the case wherein the current lead stripe has a coating on both sides, two integrated measuring transducers are used. One of them is placed in the vicinity of the first shaft guiding the stripe movement, as shown in FIG. 3. The other is placed in the vicinity of the second shaft with the same installation gap $d_0$, but relative to the surface of the coating found on the other surface of the current lead stripe, as shown in FIG. 4.

The shell of the first eddy current probe in the integrated measuring transducer forms a rectangle in section. As shown in FIG. 3, the operating surface is formed by the concave surface of the shell with the parallel current lines arranged thereon with a constant spacing. The direction of the currents in the lines is identical. The opposite convex surface of the shell with the parallel current lines of opposite direction arranged thereon is non-operating. The probe is arranged so that the direction of the current lines is the same as the movement direction of the current lead stripe.

Figure 5:
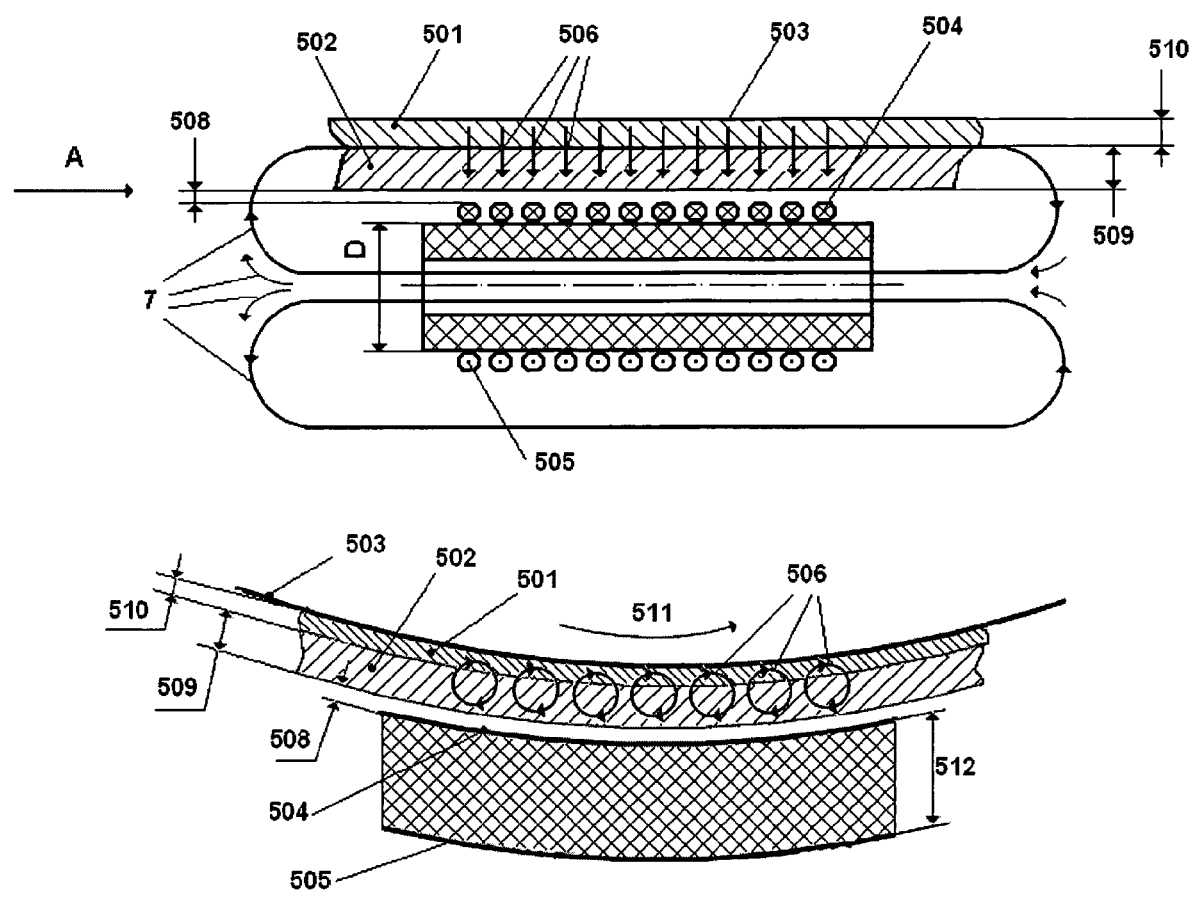
FIG. 5 shows the arrangement of the first eddy current probe relative to the current lead stripe with a coating (the figure above is a view in the movement direction of the current lead stripe with a coating, the figure below is a view in the direction that is perpendicular to the movement direction of the current lead stripe with a coating: 501 is the stripe (foil) of the current lead, 502 is the coating, 503 is the surface of the shaft guiding the movement of the current lead stripe, 504 indicates the current lines (conducting wires) on the operating surface of the probe shell, 505 indicates current lines (conducting wires) on the opposite surface of the probe shell, 506 indicates eddy currents in the foil with a coating, 507 indicates the intensity lines of the probe magnetic field, 508 is $d_0$, the installation gap value of the probes relative to the outer surface of the coating; 509 is $T_c$, coating thickness; 510 is $T_f$, the foil thickness; 511 is the direction of movement of the electrode during coating; 512 is D, the width of the probe shell.

As an informative signal of the first eddy current probe being fixed in the process of movement of the current lead stripe with the coating, the added real components of the complex impedance normalized to its inductive reactance, $R_{ad}/\omega L_0$. FIG. 5 shows in section the relative arrangement of the first eddy current probe and of the current lead stripe (foil) with a coating, as well as the direction of passing the eddy currents in the foil of the current lead with a coating.

As follows from FIG. 5, the trajectories of the eddy currents being induced in the sample by the field of the first probe cross the boundary between the foil and the coating. In this case the eddy current flows in succession through the region of the foil, the boundary and the coating region. The electrical conductance of the metallic foil is a stable value.

Therefore the value of the eddy current and the shape of each of its trajectories will depend on the contact resistance between the foil and the coating and on the specific electrical conductance of the coating.

The surface of the aluminum foil placed in an air medium is covered with a thin film of aluminum oxide ($Al_2O_3$). In the process of applying the coating onto the moving foil on the coating machine this foil gets destroyed to a substantial degree. However, as demonstrated by tests that have been carried out, film destruction during the coating operation is not complete. Additionally, for thin coatings that are not high density or high porosity the molecules of oxygen can diffuse from the air through the coating to the surface of the foil. Oxygen can also diffuse from the interior pores of the coating.

The contact resistance of the aluminum foil with a coating within the region being controlled is inversely proportional to the area of the region being controlled where there is no insulating oxide film. Hence, the larger the area of the region on which the insulating foils is destroyed, the lower the value of the contact resistance between the foil and the coating, and vice versa. In chemical power sources such as batteries and in supercapacitors the aluminum foil performs the role of a current lead that is it is intended to transfer the current into the composite coating and to receive the current there from. Therefore the value of the contact resistance has a key role in these elements, substantially determining the rate of the element charging/discharging.

If an insulating oxide film is present in a certain contact region between the foil and the coating, then the eddy current flowing in this region does not cross the boundary between the foil and the coating. In such cases two separate closed eddy current trajectories are formed. One of them is in the foil layer, and the other is in the coating layer. A similar picture is observed during the eddy current flaw detection of surface cracks in conducting materials. In this case a strap type eddy current probe is used in the form, for example, of a short cylindrical inductance coil. In such case the eddy current flowing in the material along a circular trajectory coaxial with the excitation cylindrical coil is divided by a long deep surface crack into two closed trajectories located on both sides of the crack.

In such situations as the absence of an insulating oxide film, when a common trajectory is formed of the eddy current flowing in succession through the foil layer, the boundary, the coating layer and returning into the foil, and when an insulating foil is present, when the eddy current loops are closed separately in the foil layer and separately in the coating layer without crossing the boundary. In this case, the impedance value of the eddy current probe will be different. Therefore, by fixing the components of the added impedance of the eddy current probe, it is possible to determine the presence of an insulating oxide film within the control region. The lines of force of the probe eddy magnetic field penetrating into the sample as shown in FIG. 5 induces around themselves multitudes of closed eddy current loops. Since the magnetic field that is generated by the parallel current lines arranged at an identical distance from each other and forming the operating surface of the eddy current probe have a regular character, the eddy current density within the operating control region at the boundary between the foil and the coating is constant. Hence it becomes possible to detect the presence or absence of an insulating oxide film at practically all points of the boundary surface between the foil and the coating. The total junction resistance between the foil and the coating is a function of the area value of the ohmic contact within the control region.

Experimental studies with carbon coatings, as well as with composite coatings comprised of a layer of carbon and a layer of spinel ($LiMn_2O_4$) or layer of $MnO_2$ based composite coatings have shown that the value of the added reactance of the first eddy current probe normalized compared to its inductive reactance changed very little (within 10%). A substantially wider range of change was observed for the relative added real components of the complex impedance of the probe. Therefore, it is the value of this parameter of the probe that was fixed as the informative signal.

Figure 6:
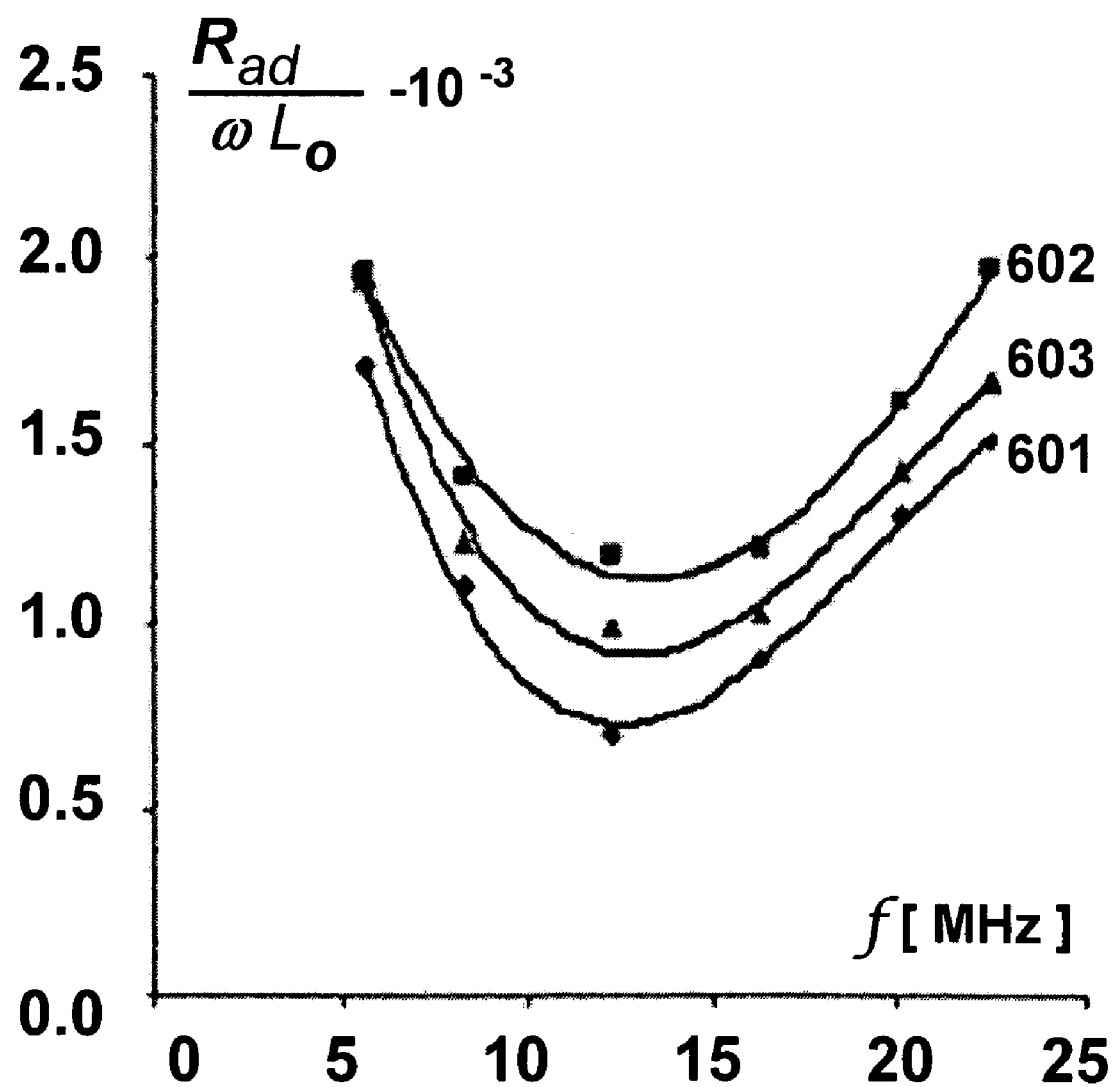
FIG. 6 shows the frequency characteristics of the relative added real components of the complex impedance of the first eddy current probe arranged over the layer of the carbon coating applied to a non-etched aluminum foil of the current lead: 601 is the non-etched (smooth) aluminum foil, thickness $T_f=25$ μm without coating, 602 is the non-etched aluminum foil with an applied carbon layer of thickness $T_c=23$ μm without compression, 603 is the non-etched aluminum foil with an applied carbon layer of thickness $T_c=23$ μm compressed with a force of 3 tons.
Figure 7:
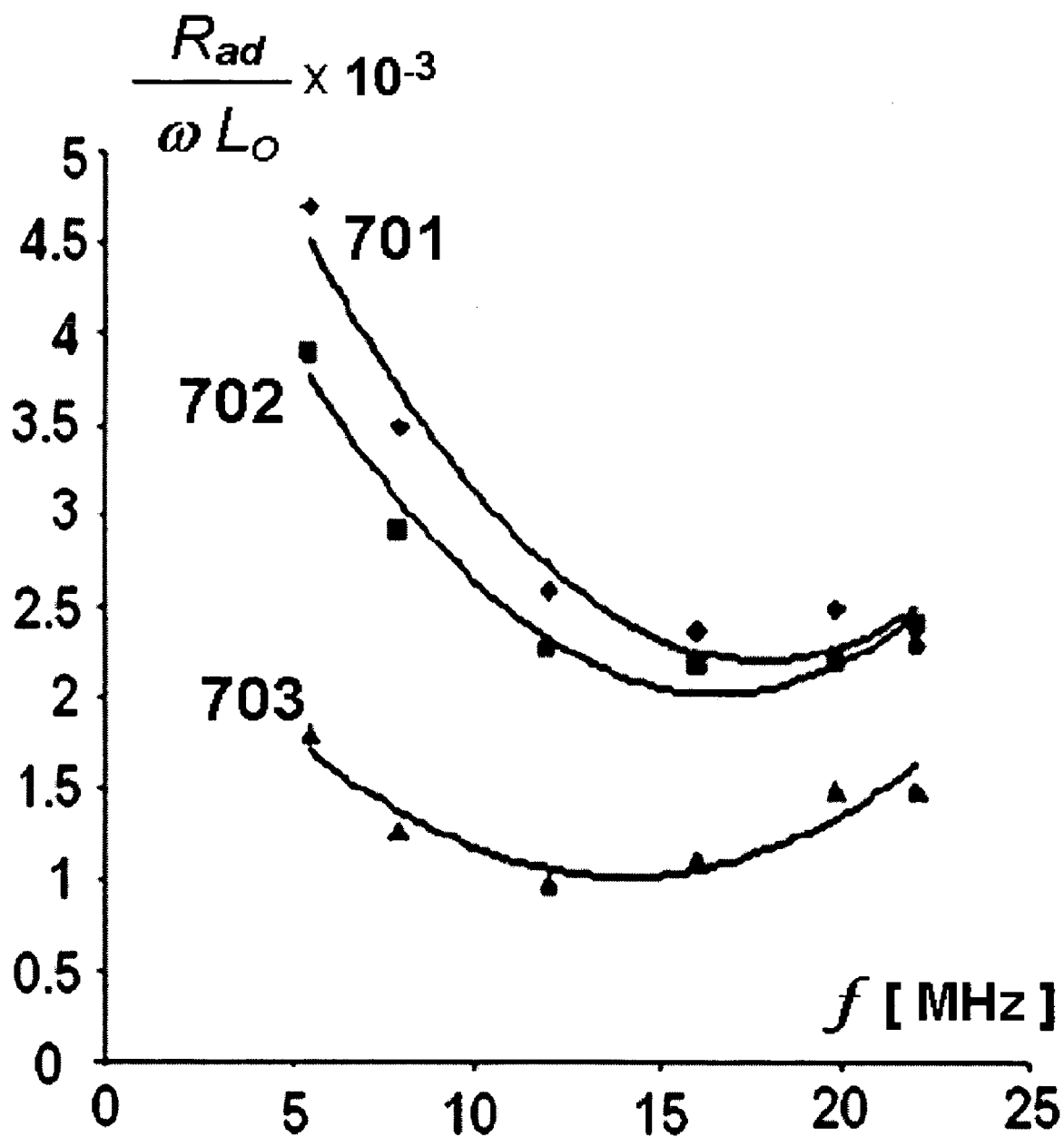
FIG. 7 shows the frequency characteristics of the relative added real component of impedance of the first eddy current probe arranged over the layer of the carbon coating applied to an etched aluminum foil of the current lead: 701 is aluminum foil etched by a chemical method with a thickness $T_f=11$ μm (after etching) without coating, 702 is etched aluminum foil with an applied carbon layer of thickness $T_c=23$ μm without compression, 703 is an etched aluminum foil with an applied carbon layer of thickness $T_c$=23 μm compressed with an force of 3 tons.

The measurement of the frequency characteristics of the relative added real components of the complex impedance of the first eddy current probe arranged over the aluminum foil with a different thickness without a coating has shown that these characteristics have their minimum. These characteristics are shown in FIG. 6 and FIG. 7. (Dependence in FIG. 6, designated by 1 was recorded for an aluminum foil with a smooth surface of thickness $T_0=25$ μm. The dependence in FIG. 7, also designated by 1, was recorded for an aluminum foil etched in an alkali and correspondingly having a rough surface of thickness $T_0=11$ μm). Besides the general extremal character of these curves it should be noted that for the smooth non-etched foil having a substantially higher thickness the value of the relative added real components of the complex impedance $R_{ad}/\omega L_0$ was, on average, more than two times lower than for the etched foil with a rough surface having a lesser thickness. These facts have the following explanation.

The reduction of the added real components of the complex impedance $R_{ad}/\omega L_0$ with the frequency increase in the pre-extremal region is related to the reduction in the eddy current pipe section reduction during its pushing to the foil surface due to the skin effect that are described in literature. In such case the value of the eddy current is reduced, with a corresponding reduction in the capacitance of the ohmic (Joule) losses that is proportional to the product of the squared current value by the real components of the complex impedance of the material ($I^2R$). This results in a reduction of the added real components of the complex impedance $R_{ad}/\omega L_0$ of the first eddy current probe.

Due to the fact that the induction coil functioning as an eddy current probe is powered by a frequency-independent current generator, the magnetic field intensity of the probe $H_0$ is maintained constant within the operating frequency range. The relative value of the added reactance or the added inductance that characterizes the intensity of the resultant eddy current circuit in the foil $H_e$, during the transition from the non-etched to etched foil changed very little, within 10%. Hence, the intensity of the total magnetic field $H_s$ determined on the basis of the electromagnetic induction law by the counteracting primary field of the coil $H_0$ and the field of eddy currents $H_e$ as $H_s=H_0-H_e$ is also stable enough. In such case it is also stable in the same degree the intensity of the electric field $E_f$ that excites the eddy current in the foil and is determined through $H_f$. This suggests that a change in the capacitance of Joule losses is caused by the change in the resistance of the sample being studied and in the frequency of the probing field.

The reduction of the value $R_{ad}/\omega L_0$ with an increase of frequency being observed in the pre-extremum region of frequency characteristics of aluminum foil samples could continue practically to zero if the frequency increase is substantial. A similar effect is observed, for example, in centimeter range waveguides with a polished copper or silver-plated surface, or in resonators where the electromagnetic wave essentially does not penetrate into the metal and attenuation approaches zero.

In our case a reduction of $R_{ad}/\omega L_0$ with the frequency is impeded by another mechanism. When the eddy current is pushed to the near-surface layers of the foil the growth of the real components of the complex impedance with the frequency becomes prevailing.

First, this occurs due to the reduction in the eddy current pipe section, and second, due to a much higher surface resistance of the foil in comparison to the volumetric value as a result of the microrelief of the surface. In such case the level of the Joule losses increases while the added real components of the complex impedance $R_{ad}/\omega L_0$ increases with increasing frequency. A similar effect is observed when "Q" of the air inductance coils having resonant frequency in the meter wave length range gets lower with increasing frequency.

A substantial increase in the foil surface roughness achieved by etching it in alkali, and a reduction in the foil thickness from 25 to 11 μm have materially increased the added real component of the complex impedance of the probe. For an etched foil with a rough surface of lower thickness ($T_0$=11 μm) the value of the relative added real components of the complex impedance $R_{ad}/\omega L_0$ is, on average, more than twice as high as for a smooth non-etched foil having a substantially higher thickness ($T_0$=25 μm; refer to the frequency characteristics for the curves with element number 601 in FIG. 6 and FIG. 7).

Figure 8:
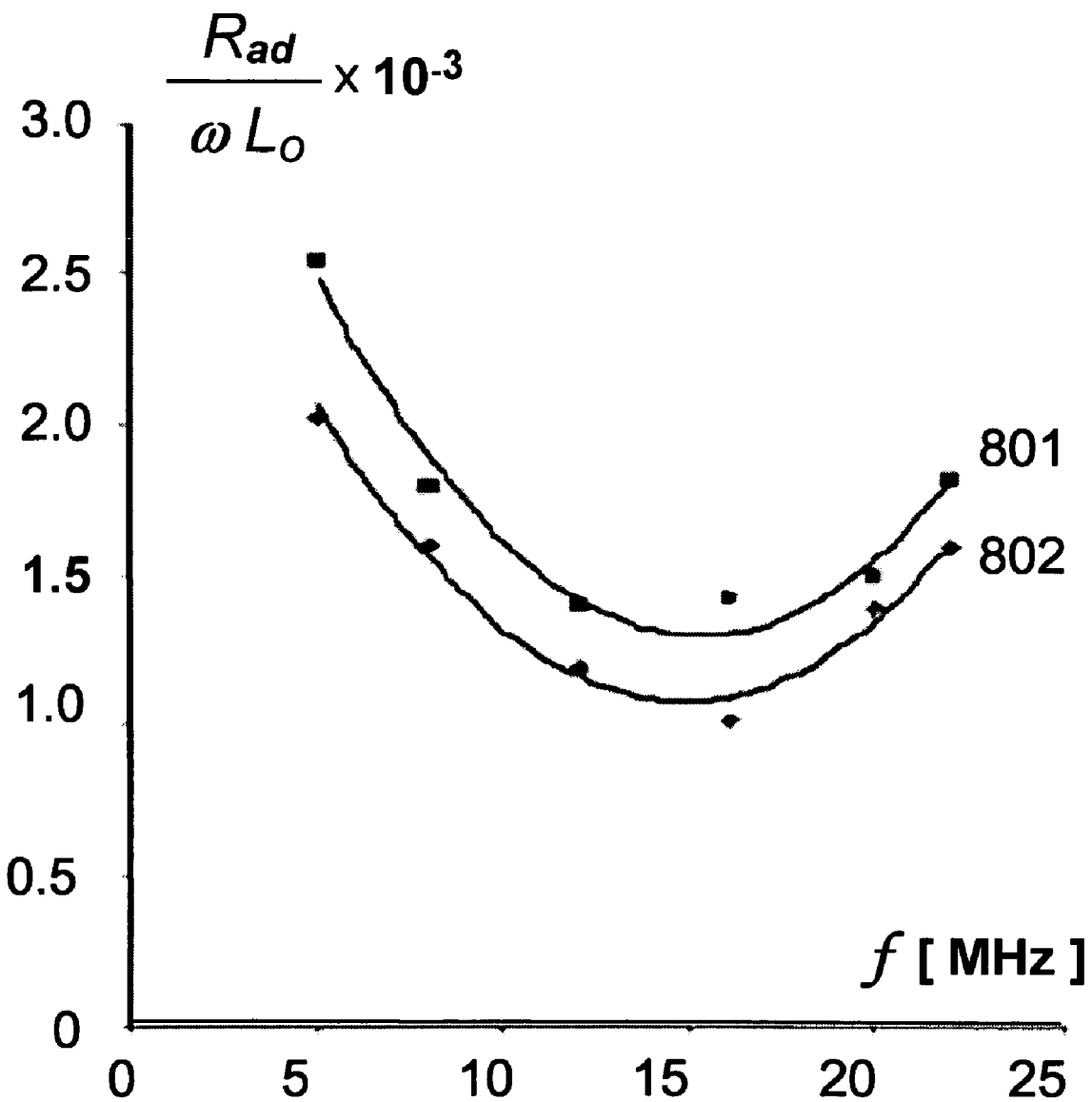
FIG. 8 shows the frequency characteristics of the relative added real components of the complex impedance of the first eddy current probe arranged over the layer of the composite coating (a $LiMn_2O_4$ spinel layer with a sub-layer of carbon) applied to the etched aluminum foil of the current lead: 801 is the etched aluminum foil with an applied composite coating comprised of a spinel layer, thickness $T_{c1}$=120 μm and a sub-layer of carbon, thickness $T_{c2}$=25 μm without compression, 802 is etched aluminum foil with an applied composite layer comprised of a spinel layer, thickness $T_{c1}$=120 μm and a sub-layer of carbon, with a thickness Tc2=25 μm compressed with a force of 3 tons.
Figure 9:
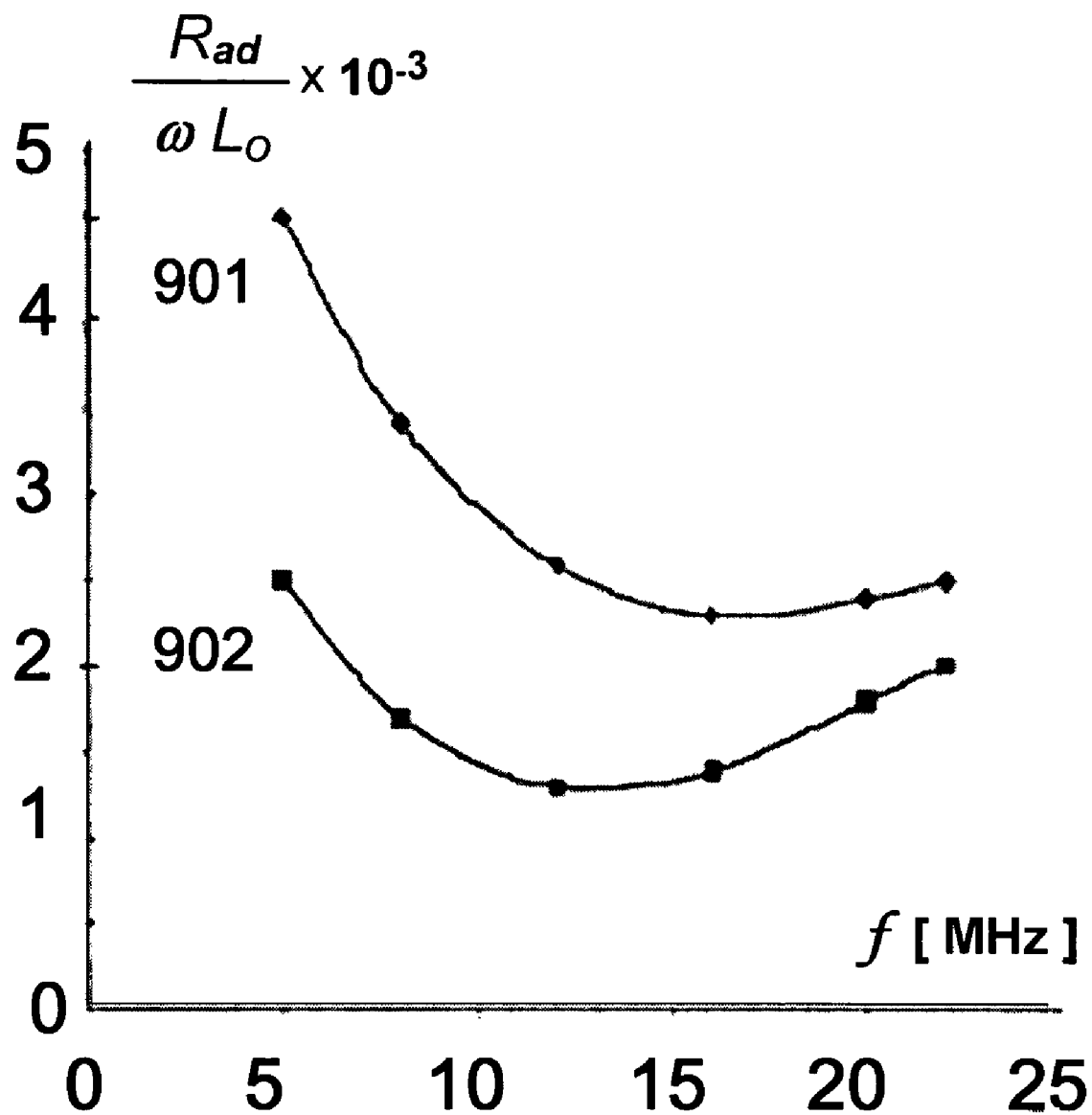
FIG. 9 shows the frequency characteristics of the relative added real components of the complex impedance of the first eddy current probe arranged over the etched aluminum foil and a layer of a composite coating applied to an etched aluminum foil of the current lead: 901 is the chemically etched aluminum foil with a thickness of $T_f$=11 μm without coating, 902 is an etched aluminum foil with an applied composite coating layer ($MnO_2$ with addition of carbon and soot) having a thickness of $T_c$=100 μm.

A form similar to the curves with number 601 in FIG. 6 and FIG. 7 have curves that correspond to the foil with a coating in the form of a layer of compressed and non-compressed carbon, as well as with more complex composite coatings whose frequency characteristics are given in FIG. 8 and FIG. 9.

The operating frequency of the first eddy current probe is selected at the point corresponding to the minimum frequency dependence of its relative added real components of the complex impedance $R_{ad}/\omega L_O$ when the probe is arranged with an installation gap $d_0$ relative to the coating surface as shown in FIG. 3. As follows from the frequency characteristics shown in FIG. 6-FIG. 9, at this frequency the influence of the surface resistance of the foil that is changed under the influence of the surface roughness does not yet have a profound effect, while the frequency is high enough to push the field to the near-surface layers of the aluminum foil, and the difference between the curves at the minimum point of approaches its maximum value.

The procedure for measurements using the first eddy current probe is as follows. Initially, and prior to the process of measurement, the first probe is placed over the surface of the current lead stripe without a coating that is arranged on the guide shaft at a distance equal to the sum of the installation gap value and the coating thickness $d_0+T_c$ (FIG. 3), and the frequency characteristics of the relative added real components of the complex impedance $R_{ad}/\omega L_o$ of the probe are measured. Then the first probe is positioned over the coating surface on the current lead stripe arranged on the guide shaft at a distance equal to the value of the installation gap $d_0$ and the frequency characteristics of the relative added real components of the complex impedance of the probe $R_{ad}/\omega L_0$ are measured again.

The frequency that corresponds to the minimum frequency characteristic $R_{ad}/\omega L_0$ when the probe is placed over the coating on the current lead stripe is determined. This is accepted as the operating frequency of the first probe. The value $R_{ad}/\omega L_0$ of the probe obtained when it is placed over the stripe without a coating is stored and subsequently used as the reference value. In the process of the measurements the difference between of the relative added real components of the complex impedance $R_{ad}/\omega L_O$ of the first probe arranged over the moving current lead stripe with a coating and the reference value is determined.

Figure 10:
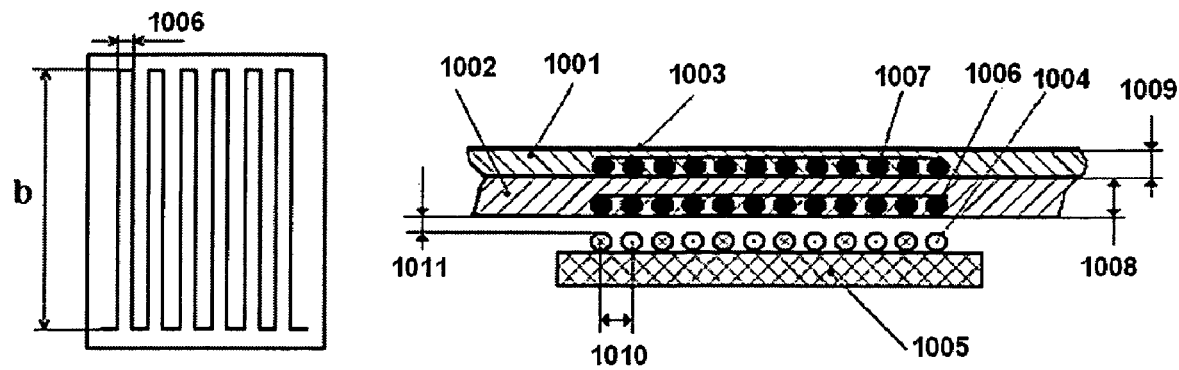
FIG. 10 shows the arrangement of the second eddy current probe relative to the current lead stripe with a coating (the figure on the right is a view in the movement direction of the current lead stripe with a coating. The figure on the left is a view of the probe operating surface): 1001 is the stripe (foil) of the current lead, 1002 is the coating, 1003 is the surface of the shaft guiding the movement of the current lead stripe, 1004 indicates the current lines (conducting wires) on the operating surface of the probe shell, 1005 is the probe shell, 1006 depicts eddy currents in the coating, 1007 is the eddy current strip in the foil of thickness $T_f$, $T_c$ indicates the coating thickness, 1011 indicates $d_0$, the installation gap value of the probes relative to the outer surface of the coating, 1010 indicates the distance between the current lines on the probe operating surface; 1012 indicates the size of the eddy current probe.

The winding of the second eddy current probe comprises a set of parallel current conductors with the opposite current direction in the adjacent conductors and with a constant distance between them (FIG. 10). The winding is arranged on the concave surface of the shell nearest to the coating. On the right in FIG. 10 the arrangement of the eddy current probe is shown relative to the current lead strip with a coating (the figure is a picture in the direction of the stripe movement).

Thus, a stripe of parallel current lines with an opposite current direction in adjacent lines functions as a source of the primary magnetic field. In FIG. 10, these current lines are designated by number 1004, the distance between them being equal to α. For each current line the current direction "in to the drawing plane" is shown with a cross while the direction "out of the drawing plane" is designated with a point. The two adjacent current lines can be presented as an elementary two-wire line, while the magnetic field of the whole probe can be calculated as a set of the fields of these two-wire lines.

The eddy currents induced by the field of the two-conductor line in the conducting medium, the outer plane boundary, which is parallel to the plane of the current lines for closed circuits in the planes, are parallel to the plane of the current lines and forms the primary probing field. In such case, the circuit with the maximum eddy current density is found directly at the boundary surface (outer surface) of the conducting medium in the maximum intensity region of the electric field.

Further the eddy current density is reduced exponentially with depth, the index or rate equation contains the product of the specific conductance of the medium as a function of the magnetic field frequency. This situation is similar to the case of exciting eddy currents in a conducting medium by means of a short cylindrical induction coil whose operating end face (the cylinder base) is parallel to the plane boundary of the medium. In such case the eddy currents form circular loops that are coaxial with the coil and whose planes are parallel to the operating end face of the cylindrical coil. The loop with a maximum eddy current density is found at the plane boundary of the conducting medium and the air space in which the coil is placed.

In FIG. 10 element number (1006) designates the maximum density eddy current lines induced by the primary field of the second eddy current probe in the coating layer. The eddy current direction in each of these lines is opposite to the current direction in the corresponding current line of the probe. Element number (1007) in the same figure designates the eddy current lines induced by the primary field of the eddy current probe in the metallic foil of the current lead. Similar to the eddy current in the coating, the direction of the eddy current in each of these lines is opposite to the current direction of the corresponding current line of the probe.

Due to the high specific electrical conductance of the metal foil and the high frequency of the probing magnetic field (the operating frequency range is within the meter wavelength range), the magnetic field of the eddy currents flowing in the foil layer has a substantial value. The inductance added into the eddy current probe with a negative sign also has a corresponding substantial value. Due to the stable geometrical parameters of the foil and its electrical conductance, the value of this added inductance is also stable. The electrical conductance of the coating material is not stable enough due to the change in the density, granulometric composition, concentration of the components, and the electrical conductance of the grains of these components.

According to the measurements, it is lower by several orders and more, (depending on the type of the coating) than the specific electrical conductance of the foil. The value of the added inductance formed by the field of the eddy currents flowing in the coating layer is marginal due to the relatively low specific electrical conductance of the coating material. Therefore the added real components of the complex impedance rated against the own inductive reactance of the probe is used as an information parameter of the second eddy current probe characterizing the specific electrical conductance of the coating material.

Examples 1 and 2 describe the field for the elementary two-wire coils of the first and the second eddy current probes, respectively.

The purpose of the second eddy current probe is to form a signal proportional to the specific electrical conductance of the coating material. Because of the small thickness of the coating and a low value of its specific conductance, in order to provide a sizable input of the coating contribution into the total value of the added real components of the complex impedance of the probe, the value that is being formed by the eddy currents flowing both in the coating and in the metallic foil, it is necessary to substantially increase the frequency of the current exciting the probe.

The eddy current probe has its own resonant frequency that is determined by its self inductance and the parasitic capacitance between the linear conductors of the probe. To preclude the influence of the probe's self resonance on the measurement process, the operating frequency of the second eddy current probe is limited at the high end by the boundary frequency that is three times lower of the frequency of the probe's self resonance.

While the frequency of the current powering the eddy current probe is increased, the added real components of the complex impedance initially increase, reaches it's maximum, and then decreases. With the increase of frequency the added imaginary part of impedance grows monotonically. This is usually reflected in the form of a hodograph on an integrated plane of the added resistance. To reduce the foil influence on the signal of the second eddy current probe its operating frequency is selected in the post-extremum region of the hodograph impedance added by the current lead stripe without coating so that the value of the added real components of the complex impedance would not exceed 10% of the hodograph maximum value.

The value of the relative real components of the complex impedance added into the second eddy current probe that is placed over the coating applied onto the foil of the current lead (FIG. 10) depends on a series of factors.

First, the primary field of the probe is attenuated by the field of the eddy currents induced in the metallic foil (the secondary field). The secondary field intensity is a function of the specific electrical conductance $\sigma_f$ and thickness $T_f$ of the metallic foil, the frequency and the distance to the source of the primary field. The secondary field intensity can be characterized by the value of the inductance added into the probe and normalized compared to the self inductance. In this case, if the probe is installed directly on the foil surface, and the frequency of the current powering the probe is increased to the boundary value, the intensity of the secondary field will be the highest and approaching to the maximum the primary field of the probe.

Correspondingly, the value of the relative inductance added into the probe will also reach its maximum. Then the value of the differential probe field, which is the operating value for the coating layer, can be determined from the difference of the two values of the probe relative added inductance. The first value is maximal and is obtained when the probe is installed on the surface of the current lead foil without coating that is found on the guide shaft, while the probe frequency is set to be equal to its boundary frequency. The second value is obtained when the probe is positioned over the foil surface also without coating, situated on the guide shaft, while the distance from the probe operating surface to the foil surface is set to be equal to the foil thickness $T_f$, and the frequency is set to be equal to its operating frequency.

The obtained difference depends only on the specific electrical conductance of the foil material $\sigma_f$, foil thickness $T_f$, the operating and boundary frequencies and practically does not depend on the electrical conductance of the low-conducting coating. Second, the total value of the real components of the complex impedance added into the second eddy current probe, which comprises the signal, depends not only on the resistance added by the eddy currents of the coating, but also on the resistance added by the eddy currents flowing in the foil of the current lead. Due to its inherent physical nature, the added real components of the complex impedance are determined by the capacitance of the Joule losses due to the flow of the eddy current in the conducting medium. The eddy currents flowing in the coating layer and in the foil are independent while their density value is determined according to the Ohm's law by the specific electrical conductance of the flow medium and by the intensity of the operating field.

Therefore the total real components of the complex impedance added into the probe can be presented as a sum of the added real components of the complex impedances. The first of these is caused by the eddy currents flowing in the coating. Its value normalized compared to self induction resistance of the probe is a function of the specific electrical conductance of the coating material $\sigma_c$, the operating frequency value $\omega$, coating thickness $T_c$ and the installation gap value $d_0$.

The second is caused by the eddy currents flowing in the foil of the current lead. Its relative value is a function of the specific electrical conductance of the foil material $\sigma_f$, the operating frequency value $\omega$, foil thickness $T_f$ and the installation gap value $d_0$.

The process of interaction between the eddy current magnetic field of the second probe and the object being tested can be described by the following equation (1)

$$\left[\frac{R_{ad}}{\omega L_0}\right]_\Sigma = \left[\lambda - \frac{L_{ad}(\sigma_f, \omega, T_f, h = T_c)}{L_0}\right] \cdot \left[\frac{R_{ad}(\sigma_c, \omega, T_c)}{\omega L_0}e^{-k\frac{d_0}{a}}\right] + \frac{R_{ad}(\sigma_f, \omega, T_f, h = T_c + d_0)}{\omega L_0}$$

where $$\lambda = \frac{L_{ad}(\sigma_f, T_f, \omega = \omega_{max}, h = 0)}{L_0}$$

and $R_{ad}$ is the real components of the complex impedance added into the probe, $L_{ad}$ is the inductance added into the probe, $L_0$ is the self inductance of the eddy current probe, $\omega$ is the operating frequency of the probe field, $\omega_{max}$ is the boundary frequency of the probe field, $\sigma_f$ is the specific electrical conductance of the foil material, $\sigma_c$ is the specific electrical conductance of the coating material, $T_f$ is the foil thickness, $T_c$ is the coating layer thickness, k is the constant coefficient experimentally determined during the change of the installation gap, $d_0$ is the installation gap value between the operating surface of the probe and the coating surface, and $a$ is the distance between the current lines (conducting wires) of the second probe.

The results of the measurements by the second eddy current probe performed using composite coatings applied onto the aluminum foil are given in Example 3.

From the total measured value of the relative added real components of the complex impedance of the second eddy current probe arranged over the moving current lead stripe with the coating, the value is subtracted from the relative added real components of the complex impedance measured at the operating frequency, while the second probe is being positioned over the surface of the stripe without the coating placed on the guide shaft at a distance equal to the sum of the installation gap value and of the coating thickness, while additive updating is being performed.

The additively updated value of the relative added real components of the complex impedance of the second probe placed over the moving current lead stripe with the coating is divided by the earlier obtained difference of the relative added inductance values thus performing a multiplicative updating.

After performing the additive and multiplicative updating procedures the value of the relative added real components of the complex impedance of the second probe caused by the eddy currents flowing in the coating layer is obtained. It is this value that is used for correcting the signal of the first eddy current probe that performs the evaluation of the resistance value between the current lead stripe and the coating layer. In this case the measurements of the first and the second probes are being synchronized taking into consideration the speed of the uniform movement of the current lead stripe with the coating in such a manner that both probes are performing measurements on the same region of the coating.

In the absence of any insulating oxide film and of air micro-gaps in the given region of the surface boundary between the foil and the coating, the closed eddy current loop crosses the boundary surface. In such case the eddy current subsequently flows through the metallic foil layer and the coating layer. Taking into consideration that the specific electrical conductance of the coating material is lower by several orders than the specific conductance of the foil metal, the total resistance to the eddy current along its trajectory (loop) will be mainly determined by the resistance of the coating region.

According to the fundamentals of the theory of eddy currents for low-conducting materials, in the initial part of the pre-extremum hodograph region of the added impedance of an eddy current probe the value of the added real components of the complex impedance is linearly dependent on the specific electrical conductance of the material. Therefore with the increasing conductance of the coating the value of the real components of the complex impedance of the first probe will increase while with the conductance reduction it will decrease. This introduces an error into the evaluation of the resistance value between the current lead foil and the coating.

The second probe signal obtained by the procedures of additive and multiplicative correction represents the relative added real components of the complex impedance caused by the eddy currents flowing only in the coating. As follows from the theory of eddy currents, this signal is proportional to the electrical conductance of the low conducting coating $\sigma_c$. In this case the procedure of correcting the signal of the first eddy current probe is carried out by multiplying its relative added real components of the complex impedance by the coefficient $\gamma = R_{ad}/R_{ad}^{(av)}$ that is the relationship of the added real components of the complex impedance of the second probe to its current average value.

Before starting the measurement cycle the multiple measurements with not less than 200 measurements being recommended by using the second probe on the current lead stripe with the coating, in order to determine the initial average value of the relative added real components of the complex impedance that is then continuously updated during the measurement cycle.

The contact resistance between the current lead stripe and the coating is evaluated by means of the first probe according to the difference between the updated value of its relative added real components of the complex impedance and the reference value obtained by measurements on the current lead stripe without a coating.

If the area of the region in the operating zone of the first probe at a given position is subdivided into the final number of N elementary regions, and the boundary between the foil and the coating within one elementary region is crossed by one elementary eddy current circuit, then the current value in the circuit will be relatively low. This is because it is mainly determined by the resistance to the current in the region of the low-conducting coating. Correspondingly, the Joule losses will be also low.

If the boundary at the elementary region is an insulating one due to the oxide film of aluminum or due to an air micro-gap, then two elementary eddy current loops are formed. The first loop is closed in the foil, and the second in the coating layer. In this case the level of the Joule losses at this region equals the sum of the losses in both loops.

The specific resistance of the foil metal is substantially lower than the specific resistance of the coating material. Therefore the total level of the losses in this case is substantially higher due to the eddy current losses in the foil. The eddy currents in the foil and in the coating that is flowing close to the boundary have different directions and attenuate one another by the interaction of their magnetic fields. Due to the much higher conductance of the metallic foil, its eddy current substantially attenuates the eddy current of the coating while it experiences essentially no influence from the current in the coating.

The total sum of the Joule losses in the operating zone of the first eddy current probe equals the sum of the losses in its elementary regions. The maximum difference of the updated value of the relative added real components of the complex impedance of the first probe and its reference value $\Delta = \Delta_{max}$ correspond to the extreme case when in all of the N elementary regions there is no insulating film or air microgap. That is, when the whole boundary provides an ohmic contact between the foil and the coating. The preliminary maximum value of this difference is found in the following manner. Before the beginning of the operating cycle of measurements not less than 400 preliminary measurements are performed on the current lead stripe with the coating in order to determine the initial minimum value of the relative added real components of the complex impedance of the first probe updated with the signal of the second probe, which is then continuously refined during the operating measurement cycle.

The zero difference of the updated value of the relative added real components of the complex impedance of the first probe and its reference value $\Delta = 0$ corresponds to the second extreme case when, for all the N elementary regions, there is no contact between the foil and the coating.

Hence, the maximum difference $\Delta_{max}$ corresponds to the minimum value of the contact resistance $R_{min}$. Then the contact resistance ratio $\eta$ in a given region $R_{con}$ to the minimum value $R_{min}$ is equal to the ratio of the maximum difference $\Delta_{max}$ to the difference determined in the given testing region:

$$\eta = \frac{R_{con}}{R_{min}} = \frac{\Delta_{max}}{\Delta_{con}} \qquad (2)$$

By specifying the tolerance, that is the upper limit of the range within which a change of the relative contact resistance value $\eta = R_{con}/R_{min}$, is allowed, the movement of value $\eta$ beyond the tolerance of value $\Delta_{max}/\Delta_{con}$ is controlled.

Figure 15:
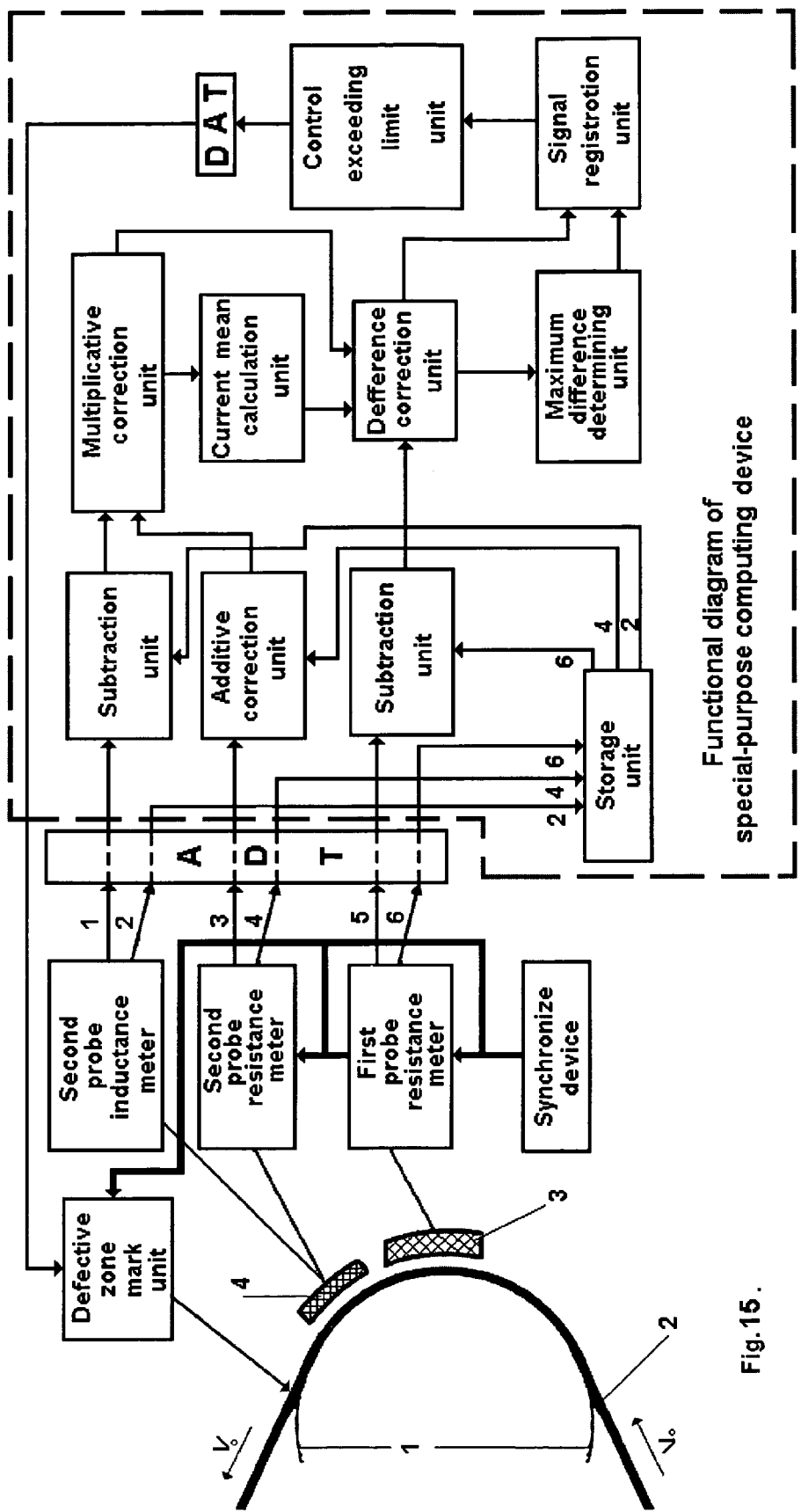
FIG. 15 is a functional diagram of a system for non-contact evaluation by the eddy current method of the present invention for determining the resistance between the current lead stripe and the coating during the fabrication of chemical power sources including batteries, supercapacitors, photovoltaic modules and the like. 1501 is the shaft guiding the movement of the current lead stripe. 1502 is the current lead stripe with a coating, 1503 is the first eddy current probe, and 1504 is the second eddy current probe.

A functional diagram of the eddy current system for non-contact evaluation of resistance between the current lead stripe and the coating in a continuous process for fabricating batteries and supercapacitors is shown in FIG. 15.

To the first eddy current probe switched into a resonant circuit, a circuit is connected for measuring the relative added real components of the complex impedance of the probe at its operating frequency. A similar circuit is connected to the second eddy current probe. The circuit for measuring the added inductance of the second probe is a two-channel one that performs measurements of the added inductance at the operating frequency of the second probe and at its boundary frequency. The output signals of these circuits in an analogue form come to the input of the three-channel analogue-to-digital converter.

The synchronizing unit connected to the circuits for measuring the added real and imaginary components of impedance of the first and the second probes. It is also connected to the unit for marking the faulty zones synchronize to the readings of the first and the second probes, taking into account the speeds of the uniform movement of the current lead stripe, so that these probes perform measurements in the same zone of the coating. After the analogue-to-digital conversion, the data enter a special calculator unit that may be either hardware or a software component. This unit contains a series of functional elements.

There is a unit for storing the values of the relative added real components of the complex impedances of the first and the second probes measured at their operating frequencies, as well as the values of the relative added inductance of the second probe measured at the boundary frequency. The values that are stored in this unit are measured initially in the region of the current lead stripe without a coating, before starting the measurement cycle. They are subsequently used during the correction procedures.

The values stored in the storage unit are used by the unit for determining the difference of the added inductance values of the second probe, by the unit additive updating of the added real components of the complex impedance of the second probe, by the unit for determining the difference of the first probe. The multiplicative updating unit actually performs the operation of division. The output signals of this unit and of the current averaging unit enter the unit for difference updating of the relative added real components of the complex impedance of the first probe and of the reference value.

The difference updating unit multiplies the current difference value by the coefficient $\gamma = R_{ad}/R_{ad}^{(av)}$ that represents the relation of the added real components of the complex impedance of the second probe after the multiplicative updating to its current average value. The output signals of the unit for current determination of the maximum updated difference for the first probe and the difference value obtained at a given location on the coated strip are forwarded to the signal recording unit.

The relation $\eta$ of the contact resistance at the given region $R_{con}$ to the minimum value $R_{min}$ that is equal to the relation of the maximum difference $\Delta_{max}$ to the difference determined at the given testing region $\Delta_{com}$ according to theory is determined and recorded in this unit.

An upper limit to the range (tolerance) within which a change in the relative contact resistance value $\eta = R_{con}/R_{min}$ is allowable is specified and this value is used by the unit for indicating when the allowable limit is exceeded.

In this unit comparison is performed of the relative contact resistance $\eta$ with this upper limit. In case the value $\eta$ moves beyond the tolerance limit, the code corresponding to the degree to which the limit is exceeded is entered into the digital-to-analogue converter. Three gradations are used to indicate to what extent the value of the relative contact resistance exceeds the corresponding limit, namely; low excess, medium excess, and substantial excess. The low excess corresponds to the excess of value $\eta$ counted from the boundary level within the 10% range, medium excess—from 10% to 30%, and substantial excess indicates greater than 30% excess.

The unit for marking the faulty zones applies corresponding marks onto the coating surface at the position where the relative contact resistance moves beyond the tolerance limits, the marks being of different colors in correspondence with the degree to which the tolerance limit is exceeded.

The first and the second probes are integrated into a single structure and are arranged in series relative to the stripe movement. The common operating surface of the probes forms a part of the surface of the cylinder with a rectangular section. Its width is limited by the maximum width of one of the probes. Its length is limited by the total length of the probes taking into account the distance between them. The total operating surface of the probes is coaxial to the surface of the current lead stripe in the region of the shaft that guides the movement of the stripe.

The shell of the first eddy current probe comprises in section of a rectangle, with the operating surface being formed by the concave surface of the shell nearest to the coating with the constant spacing parallel unidirectional current lines (conducting wires), while the non-operating surface is a convex surface of the shell with the parallel and oppositely directed current lines (conducting wires). The distance between the current lines of the first probe is selected taking into consideration the necessity to provide maximum stability of the vector potential of the probe field in the control zone. The winding of the second eddy current probe is concentrated on the concave surface of its shell nearest to the coating. The distance between the current lines of the second probe is selected taking into consideration the necessity to ensure minimum influence of the current lead foil on the value of its added real components of the complex impedance.

The ratio between the length of the current lines located on the operating surfaces of the first and the second probes, and the distance between the current lines is not less than 10. The distance between the end of the first probe and the beginning of the second eddy current probe is not less than double the width of the shell section of the first eddy current probe.

In case the current lead stripe has a coating on both sides, a pair of identical integrated measuring transducers is used, each being located in the vicinity of its guide shaft, but on a different side of the stripe coating. Each of the pair of transducers is arranged at the same distance from the lateral edge of the current lead stripe.

Several integrated measuring transducers are arranged over the surface of the coating on the current lead stripe. They are fixed on one generatrix (axis) arranged perpendicularly to the lateral edge of the current lead stripe, the distance between the transducers being identical. In case the coating is on both sides, several pairs of measuring transducers are used while the transducers arranged over one side of the coating and the transducers arranged over the opposite side are fixed on separate generatrices (axes) that are perpendicularly to the lateral edge of the stripe. The minimum distance between the lateral edge of the integrated measuring transducer and the lateral edge of the coating on the current lead stripe is not less than the height of the first eddy current probe, while the distance between the lateral edges of the adjacent integrated transducers nearest to one another is not less than double the height of the first probe.

The unit for marking the faulty zones, within which the relative value of the contact resistance between the current lead and the coating is beyond the limits of the specified tolerance, produces markings for each integrated measuring transducer separately with different colors according to the degree by which the contact resistance value exceeds the upper tolerance level.

EXAMPLES

The Examples described below are provided for illustration purposes only and are not intended to limit the scope of the invention.

Example 1

The example contains the vector potential calculation of the eddy magnetic field of an elementary two-conductor coil of the first eddy current probe.

It is known from electromagnetic field theory that the vector potential of an infinitely long current line in the direction of the coordinate axis y is described by the expression:

$$A_1 = \frac{\mu_0 I}{4\pi} \int_{-\infty}^{\infty} \frac{dy}{r_1} \qquad (3)$$

where $\mu_0 = 4\pi \cdot 10^{-7}$ H/m is the magnetic constant (magnetic permeability in vacuum), I is the current value in the line, $r_1$ is the distance from element dy to the observation point M.

In a plane perpendicular to the current line that includes an observation point M, the value $r_1$ can be expressed as:

$$r_1 = \sqrt{y^2 + \rho_1^2} \qquad (4)$$

Here y is the segment length of the current line from the point of its interception where the plane to the element $\rho_1$ is the length of the segment found in the plane and equal to the distance from the point of the plane interception with the current line to the observation point M. Taking into consideration that $$\int_{-\infty}^{\infty} \frac{dy}{\sqrt{y^2 + \rho_1^2}} = -2\ln\rho_1 \qquad (5)$$

The vector potential of an infinitely long current line in the direction perpendicular to that line equals $$A_1 = \frac{\mu_0 I}{2\pi} \ln\frac{1}{\rho_1} \qquad (6)$$

where $\rho_1$ is the length of the segment from the current line to the observation point M.

If the axes x and z of the Cartesian system of coordinates containing the observation point M are in the plane that is perpendicular to the current line, and the current line coordinates in this plane are equal to $x_1 = 1$ mm, $z_1 = 0$. Then the values of the vector potential $A_1$ are normalized against $A_0 = \mu_0 I/4\pi$, calculated in correspondence with (6) are given in Table 1.

TABLE 1

| | A/A₀ | | | | |
|---|---|---|---|---|---|
| $x_0$, mm | $z_0 = 0.1$ mm | $z_0 = 0.2$ mm | $z_0 = 0.3$ mm | $z_0 = 0.4$ mm | $z_0 = 0.5$ mm |
| 0 | −0.05 | −0.019 | −0.043 | −0.072 | −0.111 |
| 0.2 | 0.215 | 0.192 | 0.157 | 0.111 | 0.058 |
| 0.4 | 0.497 | 0.458 | 0.399 | 0.326 | 0.247 |
| 0.6 | 0.885 | 0.804 | 0.693 | 0.569 | 0.445 |
| 0.8 | 1.497 | 1.262 | 1.020 | 0.804 | 0.618 |
| 1.0 | 2.302 | 1.609 | 1.203 | 0.916 | 0.693 |
| 1.2 | 1.497 | 1.262 | 1.020 | 0.804 | 0.618 |
| 1.4 | 0.885 | 0.804 | 0.693 | 0.569 | 0.445 |
| 1.6 | 0.497 | 0.458 | 0.399 | 0.326 | 0.247 |
| 1.8 | 0.215 | 0.192 | 0.157 | 0.111 | 0.058 |
| 2.0 | −0.05 | −0.019 | −0.043 | −0.072 | −0.111 |

In Table 1, $x_0$ and $z_o$ are the coordinates of the observation point M ($x_0, z_0$). As follows from Table 1, the vector potential values along the axis x are symmetrical relative to the point $x_1 = 1$ mm at which the current line is found. At the distance $z_0 = 0.5$ mm above the current line, the vector potential equals 30% of the value that it had at the distance $z_0 = 0.1$ mm.

Figure 11:
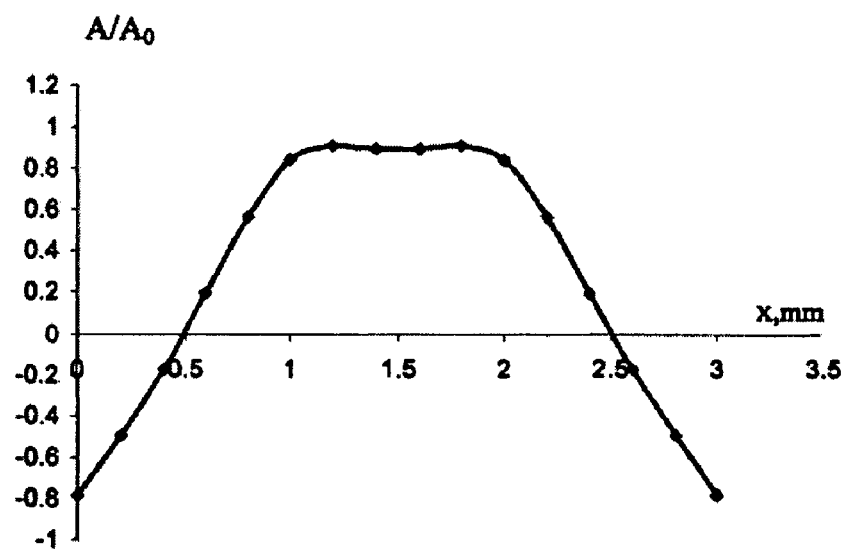
FIG. 11 depicts the change in the vector potential value of the magnetic field in the first eddy current probe comprised of two current lines (conducting wires) arranged at a 1 mm distance from each other in the direction perpendicular to these lines along x axis at the height z=0.4 mm above the plane of the two-lead line. The current lines are found at points $x_1$=1 mm, $x_2$=2 mm, $A_0=\mu_0 I/2\pi$, where $\mu_0=4\pi\cdot 10^{-7}$ H/m. "I" is the value of the electrical current in the current line.
Figure 12:
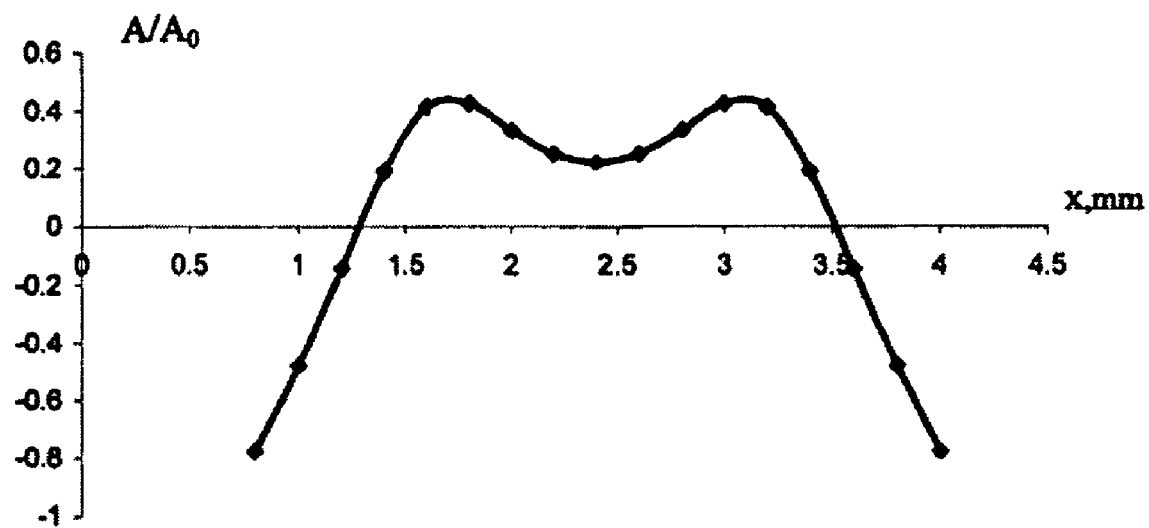
FIG. 12 depicts the change in the vector potential rated value of the magnetic field in the first eddy current probe comprised of two current lines (conductors) arranged at a 1.6 mm distance from each other in the direction perpendicular to these lines along x axis at the height z=0.4 mm above the plane of the two-lead line. The current lines are found at points $x_1$=1.6 mm, $x_2$=3.2 mm, $A_0=\mu_0 I/2\pi$, where $\mu_0=4\pi\cdot 10^{-7}$ H/m. "I" is the value of the electrical current in the current line.

In the case of an elementary two-conductor coil of the first probe, the coil is comprised of two parallel unidirectional current lines. If the current flow is in the direction of the y axis, the vector field potential in such a coil is the sum of the vector potentials of type (3). That is:

$$A = \frac{\mu_0 I}{4\pi}(-2\ln\rho_1 - 2\ln\rho_2) = \frac{\mu_0 I}{2\pi}\ln\left(\frac{1}{\rho_1 \cdot \rho_2}\right) \qquad (7)$$

where $\rho_1$ and $\rho_2$ are the distances from the first and the second current lines respectively, to the observation point M. FIG. 11 shows a change of the vector potential value of the magnetic field in the elementary two-conductor coil of the first eddy current probe whose current lines are at a 1 mm distance from each other at points $x_1 = 1$ mm, $x_2 = 2$ mm, $A_0 = \mu_0 I/4\pi$. The vector potential change is shown at the height z=0.4 mm above the plane of the current lines. This height was selected taking into consideration that the height of the installation gap $d_0 = 0.2$ mm (FIG. 5), and the coating thickness $T_c = 0.2$ mm. FIG. 12 shows a similar curve for the current lines located at points $x_1 = 1.6$ mm, $x_2 = 3.2$ mm, when the distance between the unidirectional current lines is 1.6 mm.

When comparing the curves shown in FIG. 11 and FIG. 12 the following should be noted. First, when the current lines approach each other the vector potential value in the operating zone between the current lines increases. Correspondingly, the density of the eddy current induced in the medium will also increase which, according to the Ohm's law, is proportional to the vector potential value. Second, and of special importance, the change of the vector potential is insignificant in the operating zone between the current lines located at points $x_1 = 1$ mm, $x_2 = 2$ mm (FIG. 11). Hence, the density of the eddy current that is probing the contact between the current lead foil and the coating in the operating zone of the elementary two-conductor coil of the first probe will also be constant. This cannot be said with regard to the cell with the current lines arranged at a 3.2 mm distance from each other. Here the value of the vector potential in the operating zone of the elementary cell changes by essentially two fold, and it is not reasonable to use such an eddy current in testing.

In general, when the first eddy current probe contains, on its operating surface, N parallel unidirectional current lines. The value of its vector potential is calculated by formula:

$$A = \frac{\mu_0 I}{2\pi} \sum_{k=1}^{N} \ln\left(\frac{1}{\rho_k}\right) \quad (8)$$

where $\rho_k$ is the distance from the corresponding current line to the observation point M.

Example 2

Figure 13:
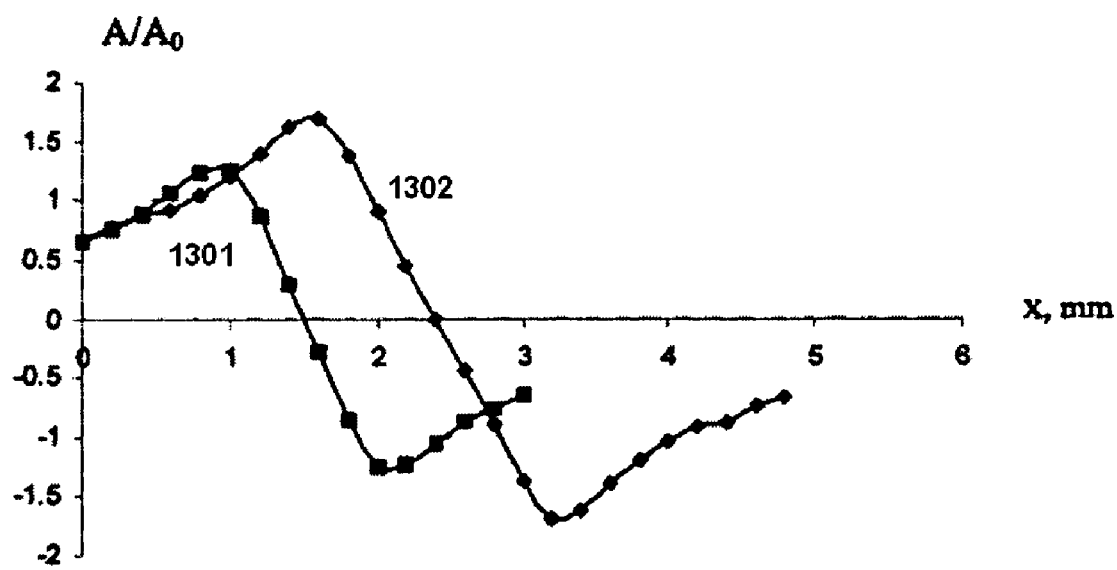
FIG. 13 depicts the change in the vector potential value of the magnetic field in the second eddy current probe comprised of two current lines in the direction perpendicular to these lines along x axis at the height z=0.3 mm above the plane of the two-lead line: curve 1301 corresponds to the current lines placed at 1 mm distance from each other at points $x_1$=1 mm, $x_2$=2 mm. Curve 1302 corresponds to the current lines found at 1.6 mm distance from each other at points $x_1$=1.6 mm, $x_2$=3.2 mm, $A_0=\mu_0 I/2\pi$, where $\mu_0=4\pi\cdot 10^{-7}$ H/m. "I" is the value of the electrical current in the current line.

In the case of the elementary two-conductor cell of the second probe; the cell is comprised of two parallel current lines with oppositely directed currents in the lines. Let us assume that the currents flow in the positive and negative directions of the y axis. The field vector potential of such a cell comprises the sum of the vector potentials of type (3) designated with opposite signs. In such case $$A = \frac{\mu_0 I}{4\pi}(-2\ln\rho_1 + 2\ln\rho_2) = \frac{\mu_0 I}{2\pi}\ln\left(\frac{\rho_2}{\rho_1}\right) \quad (9)$$

where $\rho_1$ and $\rho_2$ as before, are correspondingly the distances from the first and the second current lines to the observation point M. FIG. 13 shows a change of the vector potential value of the magnetic field in the elementary two-conductor cell of the second eddy current probe whose current lines are at a 1 mm distance from each other at points $x_1=1$ mm, $x_2=2$ mm (curve 1), and at a 1.6 mm distance from each other at points $x_1=1.6$ mm, $x_2=3.2$ mm (curve 2). The vector potential change is shown at the height z=0.3 mm above the plane of the current lines. This height was selected taking into consideration the height of the installation gap $d_0=0.2$ mm, and the coating thickness $T_c=0.2$ mm (FIG. 10).

When comparing the curves 1 and 2 in FIG. 13, it is necessary to note their two characteristic features. First, the distance between the maximum and minimum point of the vector potential for the first curve is 1 mm, and for the second curve it is 1.6 mm. Hence, in the first case the probing lines of the eddy current with maximum density in the coating layer are more frequent than in the second case. That means that the testing selectivity in the first case is higher than in the second case. Second, the maximum vector potential in its absolute value for the first curve is less by a factor of 1.36 than for the second curve. When the current lines further approach one another this trend will increase.

Table 2 contains the maximum vector potential values normalized as compared to the maximum value when z=0.1 mm depending on the height z above the surface of the two-conductor line.

TABLE 2

| | $A_{max}(z)/A_{max}(z = 0.1 \text{ mm})$ | |
|---|---|---|
| z, mm | a = 1.0 mm | a = 1.6 mm |
| 0.1 | 1.0 | 1.0 |
| 0.2 | 0.706 | 0.752 |
| 0.3 | 0.541 | 0.609 |
| 0.4 | 0.450 | 0.510 |
| 0.5 | 0.381 | 0.448 |

In Table 2, the value "a" is the distance between the current lines. As follows from Table 2, for the current lines arranged at the distance of a=1 mm from each other the vector potential value decreases faster than for the current lines arranged at the distance of a=1.6 mm. This regularity is of importance for the second eddy current probe because with the lower relative value of the vector potential in the field entering the foil layer. The lower the eddy current density in the foil and, correspondingly, the lower the relative influence of the foil on the added resistance of the second eddy current probe in comparison to the coating layer.

In a general case, when the second eddy current probe contains N parallel current lines on its operating surface, the vector potential of the probe is calculated by the formula:

$$A = \frac{\mu_0 I}{2\pi}\ln\frac{\rho_2 \cdot \rho_4 \cdot \rho_6 \cdot \ldots \cdot \rho_N}{\rho_1 \cdot \rho_3 \cdot \rho_5 \cdot \ldots \cdot \rho_{N-1}} \quad (10)$$

where $\rho_i$ (i=1 ... N) is the distance from the respective current line to the observation point M.

Example 3

This Example describes the results of measurements performed with the second eddy current probe using a composite coating applied to an aluminum foil. For comparison, the results of measurements with probes of other designs are also shown.

Probes of various designs that provide excitation of eddy currents flowing in the planes that are parallel to the surface of the current lead stripe have been studied. A composite material of composition 85% $MnO_2$, 5% carbon, 5% carbon black and 5% binder was used.

As the first design of the eddy current probe, a spiral induction coil was studied in which all the turns were in one plane. The maximum number of turns was W=16, and the outer diameter of the coil was $D_{max}=35$ mm, while the inner diameter was $D_{min}=5$ mm. The coil was wound with a copper wire of diameter $\theta_0=0.8$ mm. The turns of the coil were then unwound from its outer side while the inner coil diameter $D_{min}$ remained constant.

The methodology of measurements was the same for all the eddy current probe designs being compared. Initially the operating end face of the probe is arranged at a distance of 100 μm (installation gap $d_0$=100 μm) from the surface of the coating on the aluminum foil, the coating thickness $T_c$=100 μm, the foil thickness $T_f$=25 μm. The parameters being measured included the relative added real components of the complex impedance of the probe $[R_{ad}/\omega L_0]_c$ and the relative added inductance $[L_{ad}/L_0]_c$. Then the operating end face of the probe is placed at the distance $d=d_0+T_c=200$ μm from the foil surface without any coating and the values $[R_{ad}/\omega L_0]_f$ and $[L_{ad}/L_0]_f$ are fixed. The information parameter, as stated above, is the value $R_{ad}/\omega L_0$. The difference was determined by the relative added real components of the complex impedances $\Delta_r=[R_{ad}/\omega L_0]_c-[R_{ad}/\omega L_0]_f$ and then the relation $$\gamma_R = \frac{\left[\frac{R_{ad}}{\omega L_0}\right]_c - \left[\frac{R_{ad}}{\omega L_0}\right]_f}{\left[\frac{R_{ad}}{\omega L_0}\right]_f} \quad (11)$$

at the corresponding frequency. The obtained data for a plane spiral coil are given in Table 3 below.

TABLE 3

| The number of turns | $\Delta_r = [R_{ad}/\omega L_0]_C - [R_{ad}/\omega L_0]_f$ | $\gamma_R$, % | f, MHz |
|---|---|---|---|
| 16 | $0.21 \cdot 10^{-3}$ | 1.1 | 13.5 |
| 13 | $0.19 \cdot 10^{-3}$ | 1.26 | 16 |
| 10 | $0.22 \cdot 10^{-3}$ | 2.06 | 21 |
| 8 | $0.18 \cdot 10^{-3}$ | 2.53 | 28 |
| 5 | $0.18 \cdot 10^{-3}$ | 12.4 | 44 |

Table 4 contains corresponding data for a short cylindrical coil of diameter D=15 mm, the coil being wound with copper wire of diameter $\theta_0$=0.

TABLE 4

| The number of turns | $\Delta_r = [R_{ad}/\omega L_0]_C - [R_{ad}/\omega L_0]_f$ | $\gamma_R$, % | f, MHz |
|---|---|---|---|
| 3.5 | $0.08 \cdot 10^{-3}$ | 38.1 | 30 |

Table 5 contains corresponding data for a plane coil in the form of six linear conductors of length b=27 mm (FIG. 10). The distance between the axes of the conductors is a=3 mm, and the diameter of conductors is $\theta_0$=0.8 mm. The direction of the currents in the adjacent linear conductors is opposite.

TABLE 5

| The number of turns | $\Delta_r = [R_{ad}/\omega L_0]_C - [R_{ad}/\omega L_0]_f$ | $\gamma_R$, % | f, MHz |
|---|---|---|---|
| 3 | $0.71 \cdot 10^{-3}$ | 34.0 | 30 |
| 3 | $0.52 \cdot 10^{-3}$ | 54.1 | 40 |
| 3 | $0.40 \cdot 10^{-3}$ | 40.3 | 50 |
| 3 | $0.42 \cdot 10^{-3}$ | 69.4 | 60 |
| 3 | $0.30 \cdot 10^{-3}$ | 90.4 | 70 |

Table 6 contains corresponding data for a plane coil in the form of 24 linear conductors of length b=35 mm (FIG. 10), the distance between the axes of the conductors a=0.9 mm, diameter of conductors $\theta_0$=0.8 mm. The direction of the currents in the adjacent linear conductors is opposite.

When comparing the data shown in Tables 3 through 6, it should be noted that the maximum sensitivity $\gamma_R$ to the electrical conductance of the coating is observed in probes of the stripe type (Tables 5 and 6). However, the absolute values of the difference $\Delta_f$ are higher in Table 6. This means that the resistance values that are being measured are higher. Hence the use of the probe of the latest design is preferable.

TABLE 6

| The number of turns | $\Delta_r = [R_{ad}/\omega L_0]_C - [R_{ad}/\omega L_0]_f$ | $\gamma_R$, % | f, MHz |
|---|---|---|---|
| 12 | $0.74 \cdot 10^{-3}$ | 136.5 | 30 |
| 12 | $0.88 \cdot 10^{-3}$ | 129.4 | 40 |
| 12 | $0.93 \cdot 10^{-3}$ | 123.6 | 50 |
| 12 | $1.03 \cdot 10^{-3}$ | 92.9 | 60 |
| 12 | $1.12 \cdot 10^{-3}$ | 75.4 | 70 |

Figure 14:
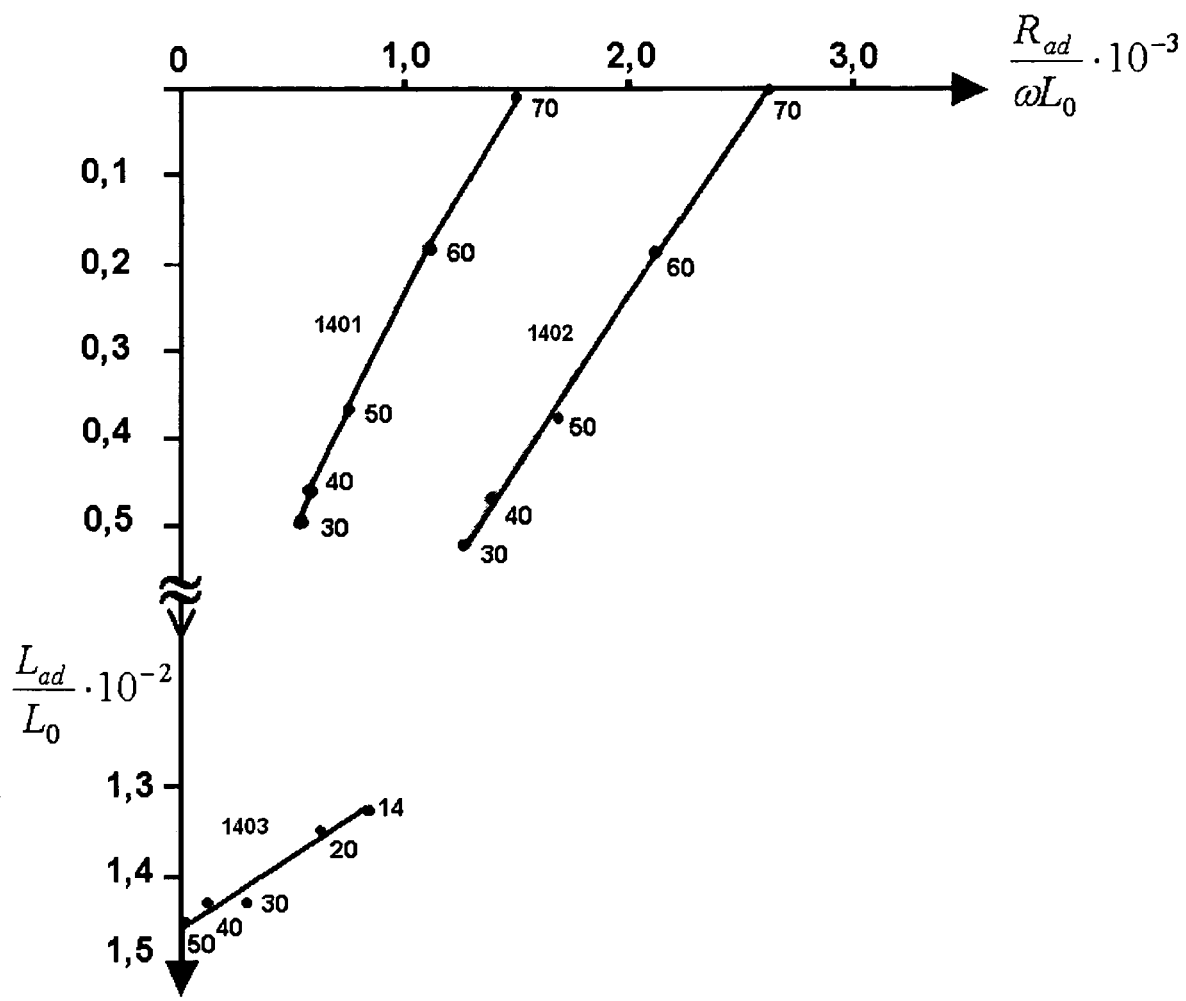
FIG. 14 shows the hodographs of the added impedance of the second eddy current probe arranged over the aluminum foil (curve 1401) and over the coating applied to the aluminum foil (curve 1402), as well as a hodograph of the short cylindrical induction coil (curve 1403). The aluminum foil has a thickness of $T_f$=25 μm. The $MnO_2$ based composite coating has a thickness of $T_c$=100 μm.

FIG. 14 contains the hodographs of the added impedance of the second eddy current probe arranged over the aluminum foil (curve 1401) and over the coating applied to the aluminum foil (curve 1402), as well as the hodograph of the short cylindrical induction coil (curve 1403). The aluminum foil thickness is $T_f$=25 μm, the $MnO_2$ based composite coating, thickness was $T_c$=100 μm. The probe is a plane coil in the form of 24 linear conductors, length b=35 mm (FIG. 10), with the distance between the axes of the conductors a=0.9 mm. The diameter of conductors is $\theta_0$=0.8 mm.

The direction of the currents in the adjacent linear conductors is opposite. The digits near the points designate the frequencies of the eddy magnetic field of the probe. A comparison of the points corresponding to the identical frequencies on the curves 1001 and 1002 shows that the added inductance is practically unchanged. That is, the low-conducting coating does not actually influence the field intensity of the probe. Also shown in FIG. 14 for comparison is the hodograph line for the short cylindrical coil with diameter D=15 mm and width W=3.5. The coil is wound with copper wire having a diameter $\theta_0$=0.8 mm.

Example 4

This Example describes results of the measurements performed with an eddy current probe of the first type on samples of the chemically etched initial foil, as well as the foil of the first and the second type with a carbon layer applied thereon. In one case the carbon layer was applied without compression. In the other case the coating was applied with a subsequent compression step. The foil was etched in an alkali solution. The carbon layer was prepared on the base of a PVDF binder.

The framework of the eddy current probe used for taking the measurements forms a rectangle of 25×10 mm, with a length of 35 mm. On the operating surface of the shell were arranged six straight parallel conductors from copper circular cross section of identical length l=35 mm. The distance between the axes of the conductors is a=3.5 mm. The diameter of the conductor is $\theta_0$=1 mm.

The results of the measurements are given in FIG. 6 and FIG. 7. FIG. 6 in particular shows the frequency characteristics of the relative added real components of the complex impedance of the probe located over the coating layer of carbon applied on the non-etched aluminum foil of the current lead. The element 601 represents the non-etched (smooth) aluminum foil with a carbon layer applied thereon. The thickness of the carbon layer is $T_f$=25 μm without a coating. 602 is the non-etched aluminum foil with a carbon layer of thickness $T_c$=23 μm without compression. 603 is the non-etched aluminum foil with a carbon layer applied thereon with a thickness of $T_c$=23 μm, and compressed with a force of 3 tons.

FIG. 6 shows that the samples with the carbon layers give higher values of $R_{ad}/\omega L_0$ than the smooth non-etched foil. The explanation may be as follows. Eddy currents in the foil and in the coating form their own closed trajectories. A common closed eddy current loop crossing the boundary between the foil and the coating is not formed, and this is probably related to the presence of an insulating aluminum oxide film on the foil surface. In such case the Joule losses due to the eddy current flow in the carbon layer are added to the losses in the foil, thus increasing the added real components of the complex impedance $R_{ad}/\omega L_0$. It is of interest to note that the compressed carbon layer that has a higher conductance due to the higher carbon density gives lower $R_{ad}/\omega L_0$ values than the non-compressed layer. This effect seems to be related to the fact that the carbon layer compression disturbs to some degree the integrity of the oxide foil, and the eddy currents penetrate into the carbon layer.

FIG. 7 shows the frequency characteristics of the relative added real components of the complex impedance of the probe arranged over the carbon coating layer applied onto the: 1—chemically etched aluminum foil of thickness $T_f$=11 μm (after etching) without a coating, 2—chemically etched aluminum foil with an applied thereon carbon layer, thickness $T_c$=23 µm without compression, 3—chemically etched aluminum foil with an applied thereon carbon layer, thickness $T_c$=23 µm, compressed with a force of 3 tons.

As it is shown in FIG. 7, when the graphite layer is placed on the etched aluminum foil a different situation is observed in comparison to FIG. 6. Here the curves for the non-compressed graphite layer (curve 702) and for the compressed graphite layer (curve 703) are located under the frequency characteristic for the etched aluminum foil in the region of the lower values of the added real components of the complex impedance. This indicates the formation of multiple eddy current loops that are crossing the boundary between the foil and the carbon layer. In this case the current successively flows in the layer of aluminum and the layer of graphite. This is especially clearly seen when comparing the characteristics of 701 and 703 corresponding to the etched foil and the compressed graphite on that foil.

A reduction of the added real components of the complex impedance during the transition from curve 701 to curve 703 is related to the reduction of the eddy current value due to the fact that the common current trajectory includes a section with a higher resistance (carbon). In such case the level of the real components of (Joule) losses determined as the product of the squared eddy current value times the resistance ($I^2R$) of the material along the current flow trajectory is reduced due to the reduction of the squared current value.

The non-compressed carbon layer (curve 702) seems to have a smaller area of contact with the etched surface of the aluminum foil characterized by an increased roughness, while there is a number of a section where there is no ohmic contact.

Correspondingly, part of the total eddy current in the foil is enclosed therein and does not cross the boundary.

Example 5

This Example describes the measurements with an eddy current probe of the first type performed on samples of etched aluminum foil with a composite coating applied thereon. The probe parameters are the same as in Example 4.

FIG. 8 shows the frequency characteristics of the relative added real components of the complex impedance of the first eddy current probe placed over the layer of the composite coating ($LiMn_2O_4$ spinel layer with a carbon sublayer), applied onto the etched aluminum foil of the current lead. 801 is the etched aluminum foil with a composite coating applied thereon and comprised of a spinel layer with a thickness of $T_{c1}$=120 µm and a carbon sublayer of thickness $T_{c2}$=25 µm without compression. 802 is the same, but the carbon sublayer has a thickness of $T_{c2}$=25 µm and is compressed with a force of 3 tons.

A comparison of the characteristics of 801 and 802 in FIG. 8 shows that in this case too, the compression of the carbon layer on the etched foil, featuring an increased roughness, provides a larger area of ohmic contact with the current lead.

It known from lithium battery technology that a reduction in the contact resistance between the aluminum current collector and the material of the composite coating presents a key problem for increasing the charging/discharging rate of a power source. A passivating film that is formed on the surface of the aluminum current collector has an insulating effect, and the current flowing through the passivating film is concentrated at any fault points in the film. Therefore, in order to increase the charging/discharging rate of a power source, it is necessary to increase the number of the point type faults in the passivating film, as well as the number of the points of contact through these faults. This is, to a large extent, achieved by introducing a sublayer of carbon on the surface of the current collector. This is confirmed by the experimental data obtained.

Example 6

This Example deals with the results of measurements with an eddy current probe of the first type that have been performed on the samples of the initial and etched aluminum foil with a composite coating applied thereon. The probe parameters are given in Example 4.

FIG. 9 shows the frequency characteristics of the relative added real components of the complex impedance of the first eddy current probe placed over the etched aluminum foil and the layer of a composite coating applied onto the etched aluminum foil of the current lead. Element 901 is the chemically etched aluminum foil with a thickness of $T_f$=11 µm without a coating. 902 is etched aluminum foil with an applied composite coating layer, of thickness $T_c$=100 µm. The composite coating is comprised of a $MnO_2$ material with an ion conductance, carbon and soot additives.

The specific electrical conductance of the composite coating material is substantially lower than the conductance of carbon. Therefore when the coating is applied onto a non-etched aluminum foil the values of the relative added real components of the complex impedance of the probe $R_{ad}/\omega L_0$ measured in the frequency range were essentially no different from similar values obtained for non-etched foil without a coating. The picture differed when a coating was applied onto a non-etched foil with a substantial surface roughness. This is illustrated by FIG. 9 where the frequency characteristic 902 that refers to the foil with a coating was located much lower than the frequency characteristic 901 for the foil without a coating. This indicates the existence of an ohmic contact over a substantial area between the current lead and the composite coating.

CLOSURE

While various embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method and eddy current system for a non-destructive, non-contact determination of resistance between the current lead stripe and the coating during the fabrication of chemical power sources including batteries, supercapacitors, photovoltaic cells and the like, said method comprising the steps of:

placing an integrated measuring transducer over the surface of the coating on a metallic current lead stripe in the region of the shaft guiding the stripe movement so that all the points on the operating surface of the transducer are found at an identical distance from the stripe surface;

measuring the relative effective resistance of the first eddy current probe of the integrated measuring transducer whose operating surface current lines are parallel to each other and are directed along the direction of movement of the current lead stripe, with the direction of the currents in the parallel wires lines being identical;

selecting an operating frequency for the first eddy current probe that corresponds to the minimum frequency dependence of its added real component of the complex impedance;

measuring the relative added real component of the complex impedance of the second eddy current probe of the integrated measuring transducer whose operating surface current lines are parallel to each other and are directed along the direction of movement of the current lead stripe, with the direction of the current flow in adjacent parallel lines being opposite;

selecting an operating frequency of the second eddy current probe in the post-extremum region of the hodograph of the impedance added by the current lead stripe without a coating so that the value of the added real component of the complex impedance would not exceed 10% of the maximum value;

detecting the value of the relative added real component of the complex impedance of the second eddy current probe caused only by the eddy currents flowing in the coating layer;

synchronizing the measurements of the first and the second eddy current probes taking into consideration the speed of the uniform movement of the current lead stripe so that both probes would perform measurements on the same area of the coating;

updating the value of the relative added components of the complex impedance measured with the first eddy current probe using the detected values of the introduced effective resistance of the second probe;

determining the value of the contact resistance between the current lead stripe and the coating at various points along the stripe as it moves over the guide shaft while using the updated values of the relative added real component of the complex impedance of the first eddy current probe.

2. Method as in claim 1, wherein the first eddy current probe is positioned over the coating surface on the current lead stripe arranged on the guide shaft at a distance equal to the installation gap value, while measuring the frequency characteristics of the relative added real component of the complex impedance and the frequency which corresponds to the minimum frequency characteristic of the relative added real component of the complex impedance, while the first eddy current probe is positioned over the coating on the current lead stripe is determined, and the frequency being accepted as the operating frequency of the first probe.

3. Method as in claim 1, wherein the first eddy current probe is positioned over the surface of the current lead stripe without a coating, the stripe being placed on the guide shaft at a distance equal to the sum of the installation gap value and the coating thickness, while measuring the frequency characteristics of the added real component of the complex impedance relative to its own inductive reactance, wherein the relative added real component of the complex impedance of the first eddy current probe being obtained with the latter positioned over the stripe without a coating and corresponding to the operating frequency, is stored and being subsequently used as a reference value.

4. Method as in claim 2, wherein during the measurement process, the difference between the relative added real component of the complex impedance of the first eddy current probe placed over the moving current lead stripe with a coating, and of the reference value which is the signal from the first eddy current probe, is determined.

5. Method as in claim 1, wherein the second eddy current probe is positioned over the current lead stripe without a coating, the stripe being arranged on the guide shaft at a distance equal to the sum of the installation gap value and of the coating thickness, while the value of the relative added real component of the complex impedance of the eddy current probe is measured at its boundary frequency, where after the second eddy current probe is positioned at a distance equal to the coating thickness, while the value of the relative added inductance of the second eddy current probe is measured at its boundary frequency, where after the second eddy current probe is positioned at a surface on the guide shaft while the relative added inductance of the eddy current probe is measured at the boundary frequency wherein the boundary frequency of the second eddy current is three times lower of the own resonant frequency of the probe.

6. Method as in claim 5, wherein the value difference of the relative added inductance of the second eddy current probe measured on the current lead stripe with a zero gap at the boundary frequency, and with an air gap equal to the coating thickness, at the operating frequency is determined.

7. Method as in claim 5, wherein from the value of the relative real component of the complex impedance of the second eddy current probe positioned over the moving current lead stripe with a coating is subtracted from the value measured at the operating frequency while the second eddy current probe is positioned over the surface of the stripe without a coating at a distance equal to the sum of the installation gap value and the coating thickness, while additive updating is carried out.

8. Method as in claim 7, wherein the additively updated impedance values of the second probe are divided by the obtained difference of the relative added inductance values of the second probe, with multiplicative updating being performed and by using the multiplicatively updated values of the relative added real component of the complex impedance of the second probe and taking into consideration the installation gap, the values for the added real component of the complex impedance caused by the eddy currents flowing only in the coating layer are obtained.

9. Method as in claim 1, wherein before the start of the measurement cycle the multiplicity of the preliminary measurements are performed with the second probe on the current lead stripe with a coating in order to determine the initial average value of the relative real component of the complex impedance of the coating due to the by the eddy currents and subsequently updated during the measurement cycle.

10. Method as in claim 1, wherein the signal of the first eddy current probe is updated by multiplying it by the coefficient $\gamma = R_{ad}/R_{ad}^{(av)}$ that comprises the ratio of the real component of the complex impedance of the second probe added by the currents of the coating to its current average value.

11. Method as in claim 1, wherein before the start of the measurement cycle, the multiplicity of the preliminary measurements are performed on the current lead stripe in order to determine the initial maximum signal value of the first probe updated by the signal of the second probe that is thereby subsequently refined during the measurement cycle.

12. Method as in claim 1, wherein the value of the contact resistance between the current lead stripe and the coating is determined according to the ratio of the updated maximum signal values of the first probe to the signal at the given position along the lead stripe, which is proportional to the ratio between the contact resistance at a given position along the lead stripe and its averaged minimum value wherein a tolerance is specified, that is the upper limit of the range within which a change of the relative contact resistance value is allowed.

13. An eddy current system for non-destructive non-contact determination of the resistance between the current lead stripe and the coating during the fabrication of chemical power sources including batteries, supercapacitors, photovoltaic modules and the like, said system comprising:

means for measuring the relative added real component of the complex impedance of the first eddy current probe of an integrated measuring transducer at its operating frequency;

means for measuring the relative added real component of the complex impedance of the second eddy current probe at its operating frequency;

means for measuring the relative added inductance of the second eddy current probe at its operating and boundary frequencies;

means for three-channel analogue-to-digital conversion of signals;

a data storage unit;

means for synchronizing the measurements of the first and the second probes;

a unit for determining the difference between the relative added real component of the complex impedance of the first probe and the reference signal;

a unit for determining the values difference of the relative added inductance of the second probe measured on the current lead stripe with a zero gap at the boundary frequency, and with an air gap equal to the coating thickness, at the operating frequency;

a unit for additive updating of the relative added real component of the complex impedance of the second eddy current probe;

a unit for multiplicative updating of the relative added real component of the complex impedance of the second eddy current probe;

a unit for continuous averaging of the updated values of the relative added real component of the complex impedance of the second probe;

a unit for updating the difference of the relative added real component of the complex impedance of the first probe and the reference signal by using the updated values of the second probe signal;

a unit for continuous determining of the maximum updated difference for the first probe;

a unit for evaluating and recording the contact resistance between the current lead stripe and the coating at the position along the lead stripe where the measurements are made;

a unit for detecting and signaling out-of-tolerance measurement results;

a digital-to-analogue converter;

a unit for marking out of tolerance fault zones along the surface of the coating.

14. Method as in claim 13, wherein the first and the second probes are integrated into a single structure and are arranged in series relative to the stripe movement, and wherein their common operating surface is a part of the cylinder surface of rectangular section with a width limited by the maximum width of one of the probes, and with a length limited by the total length of the probes taking into consideration the distance between them and wherein the common operating surface of the probes is coaxial to the surface of the current lead stripe in the region of the shaft guiding the stripe movement.

15. Method as in claim 13, wherein the shell of the first eddy current probe in section presents a rectangle, while the operating surface is formed by the concave surface of the shell, nearest to the coating, with the arranged thereon with a constant spacing parallel unidirectional current lines, and the non-operating surface is formed by the convex surface of the shell with the arranged thereon parallel current lines of the opposite direction wherein the distance between the current lines of the first probe is selected taking into regard the necessity of providing a maximum constant vector potential of the probe field within the control zone.

16. Method as in claim 13, wherein the winding of the second eddy current probe is concentrated on the concave surface nearest to the coating of the framework and presents a set of parallel current lines with oppositely directed currents in the adjacent lines and with a constant distance between them wherein the distance between the current lines of the second probe is selected taking into account the necessity to provide minimum influence of the current lead foil on the value of its added real component of the complex impedance.

17. Method as in claim 13, wherein the ratio between the length of the current lines arranged on the operating surfaces of the first and the second probes and the distance between the current lines is not less than 10, and wherein the distance between the end of the first probe and the beginning of the second probe is not less than the double width of the framework section of the first eddy current probe.

18. Method as in claim 13, wherein in the case that the current lead stripe has a coating on both sides, a pair of identical integrated measuring transducers is used, each being located in the vicinity of its guide shaft, but over the opposite sides of the stripe coating wherein each of the pair of integrated measuring transducers is positioned at the same distance from the lateral edge of the current lead stripe.

19. Method as in claim 13, comprised of several integrated measuring transducers arranged over the coating surface on the current lead stripe, fixed on one generatrix arranged perpendicularly to the lateral edge of the current lead stripe, wherein the distance between the transducers is identical and wherein the minimum distance between the lateral edge of the integrated measuring transducer and the lateral edge of the coating on the current lead stripe is not less than the height of the first eddy current probe, while the distance between the lateral edges of adjacent integrated transducers is not less than the double height of the first probe.

20. Method as in claim 13, wherein, in the case that the current lead stripe has a coating on both sides, several pairs of measuring transducers, with one set of measuring transducers arranged over one side of the coating and another set of identical measuring transducers arranged over the opposite side, are fixed on separate generatrices arranged perpendicularly to the lateral edge of the stripe.

\* \* \* \* \*